United States Patent
Weber et al.

(10) Patent No.: US 10,067,089 B2
(45) Date of Patent: Sep. 4, 2018

(54) FREE-FLOW ELECTROPHORESIS METHOD FOR SEPARATING ANALYTES

(71) Applicant: FFE SERVICE GMBH, Feldkirchen (DE)

(72) Inventors: Christoph Weber, Kirchheim (DE); Gerhard Weber, Kirchheim (DE)

(73) Assignee: FFE SERVICE GMBH, Feldkirchen (DE)

( * ) Notice: Subject to any disclaimer, the term of this patent is extended or adjusted under 35 U.S.C. 154(b) by 14 days.

(21) Appl. No.: 14/902,402

(22) PCT Filed: Jul. 4, 2014

(86) PCT No.: PCT/EP2014/001849
§ 371 (c)(1),
(2) Date: Dec. 31, 2015

(87) PCT Pub. No.: WO2015/000600
PCT Pub. Date: Jan. 8, 2015

(65) Prior Publication Data
US 2016/0238560 A1     Aug. 18, 2016

(30) Foreign Application Priority Data
Jul. 4, 2013   (EP) .................................... 13003394

(51) Int. Cl.
*G01N 27/447*     (2006.01)

(52) U.S. Cl.
CPC . *G01N 27/44795* (2013.01); *G01N 27/44769* (2013.01)

(58) Field of Classification Search
CPC .............................................. G01N 27/44769
See application file for complete search history.

(56) References Cited

U.S. PATENT DOCUMENTS

| 5,275,706 A | * | 1/1994 | Weber .............. G01N 27/44769 |
| | | | 204/450 |
| 8,449,744 B2 | | 5/2013 | Nissum |

(Continued)

FOREIGN PATENT DOCUMENTS

| WO | 2008155420 A1 | 12/2008 |
| WO | 2009062967 A1 | 5/2009 |

OTHER PUBLICATIONS

Kim et al., "Development of a novel ampholyte buffer for isoelectric focusing: electric charge-separation of protein samples for x-ray crystallography using free-flow isoelectric focusing," Acta Cryst. (2005) D61, 799-802.*

(Continued)

*Primary Examiner* — Alexander Stephan Noguerola
(74) *Attorney, Agent, or Firm* — Rossi, Kimms & McDowell LLP

(57) ABSTRACT

The present invention is related to a free-flow electrophoresis method for separating at least one analyte of interest from a mixture of analytes, wherein the method uses a separation medium comprising two or more individual separation media, wherein the two or more individual separation media differ in their pH value, and wherein each of the two or more individual separation media comprise at least one anion of at least one acid and at least one cation of at least one base, wherein the at least one acid is the same in each of the two or more individual separation media and the at least one base is the same in each of the two or more individual separation media.

18 Claims, 11 Drawing Sheets

(56) References Cited

U.S. PATENT DOCUMENTS

2004/0050697 A1     3/2004    Eckerskorn et al.
2004/0101973 A1     5/2004    Weber
2013/0134042 A1     5/2013    Weber et al.

OTHER PUBLICATIONS

Zhan et al, "Development of a simple ampholyte-free isoelectric focusing slab electrophoresis for protein fractionation," Journal of Chromatography A, 1216 (2009) 2928-2933.*
Sigma product information for hemoglobin, published Nov. 15, 1996.*
Sigma-Aldrich product information for albumin from bovine serum, published May 2, 2000.*
International Search Report issued in PCT/EP2014/001849 on Sep. 12, 2014.
Written Opinion issued in PCT/EP2014/001849 on Sep. 12, 2014.

\* cited by examiner

FREE-FLOW ELECTROPHORESIS METHOD FOR SEPARATING ANALYTES

BACKGROUND OF THE INVENTION

Field of the Invention

The present invention is related to a free-flow electrophoresis method for separating at least one analyte of interest from a mixture of analytes, a kit for carrying out the free-flow electrophoresis method and a device for carrying out the free-flow electrophoresis method for separating analytes.

Description of Related Art

Free-flow electrophoresis (FFE) is a powerful technique for the separation of a broad range of analytes, including molecules and particles. The basic principle underlying FFE is such that a separation medium flows through a separation chamber in a flow direction, whereby upon application of an electric field in the separation medium by an anode and a cathode the analytes are separated from each other. The anode and the cathode are located at a distance from each other and the separation medium flows between the anode and the cathode.

In accordance therewith, the device used for or suitable for use in FFE comprises a separation chamber through which the separation medium flows and which is a space defined by a floor and a cover and spacers separating these two from each other. In addition, such FFE device encompasses a pump for supplying the separation medium which enters the separation chamber via medium feed lines and leaves the chamber via outlets. The FFE apparatus also includes the electrodes for applying an electric field within the separation medium and one or several sample injection points for adding an analyte or a mixture of analytes which preferably contains an analyte of interest, and fractionation points for removing, among others, the analyte of interest, and mixture of analytes from which the analyte of interest has been at least partially removed, whereby the analyte of interest and the mixture of analytes from which the analyte of interest has been at least partially removed, are separated by FFE in the separation medium. In order to exert an influence upon the separation medium flow profile provision can be made for two or more separate dosage pump feed lines to add medium which are connected to the separation chamber in the vicinity of the fractionation points in the vicinity of the electrodes.

Such device for FFE and a method of FFE making use of such device is, for example, described in international patent application PCT/EP01/14408 (WO 02/50524).

Separation efficiency of FFE is influenced by various physical and electrochemical factors. These physical and electrochemical factors contribute to the broadening of the analyte bearing bands in FFE, and encompass thermal convection, electroendosmosis, broadening of the laminar flow profile and kinetic and electrokinetic effects, depending on the particular free-flow electrophoresis technique used.

The effects arising from thermal convection which are typically only observed in case of vertical orientation of the separation chamber containing the separation medium, can be avoided by changing the orientation of the separation chamber to horizontal orientation. The effects arising from electroendosmosis at the interface of a solid material such as the inner wall of the separation chamber and a liquid medium such as the separation medium can be reduced by selecting a suitable material for the separation chamber such as apolar plastic material, and/or by adding one or several surfactants to the separation medium which is known as "dynamic coating". Electrodispersion will deteriorate the separation profile in case of a concentration of ionic analytes which is enhanced relative to the concentrations of the ions used in the forming of the separation medium.

Despite tremendous progress having been made in the field of FFE, there is a need in the art for improving FFE further. Therefore, a problem underlying the present invention is the provision of a free-flow electrophoresis method which is superior to free-flow electrophoresis methods of the prior art. A further problem underlying the present invention is the provision of a free-flow electrophoresis method avoiding broadening of bands, in particular broadening of bands bearing one or several analytes. A still further problem underlying the present invention is the provision of a kit for carrying out such free-flow electrophorese method. It is also a problem underlying the present invention to provide a device for carrying out such free-flow electrophoresis method for separating analytes.

SUMMARY OF THE INVENTION

These and other problems are solved by the subject matter of the attached independent claims. Preferred embodiments may be taken from the attached dependent claims.

Furthermore, the problems underlying the present invention are solved in a first aspect which is also a first embodiment of the first aspect, by a free-flow electrophoresis method for separating at least one analyte of interest from a mixture of analytes, wherein the method comprises
  flowing a separation medium through a separation chamber in a flow direction;
  applying an electric field in the separation medium by an anode and a cathode, wherein the anode and the cathode are located at a distance from each other and the separation medium flows between the anode and the cathode, and applying the mixture of analytes to the separation medium, whereupon the at least one analyte of interest is separated from the mixture of analytes,
or
  applying the mixture of analytes to the separation medium, and applying an electric field in the separation medium by an anode and a cathode, wherein the anode and the cathode are located at a distance from each other and the separation medium flows between the anode and the cathode, whereupon the at least one analyte of interest is separated from the mixture of analytes;
  collecting fractions of the separation medium with at least one fraction comprising the at least one analyte of interest separated from the mixture of analytes;
characterized in that
the separation medium comprises two or more individual separation media, wherein the two or more individual separation media differ in their pH value, and wherein preferably each of the two or more individual separation media comprise at least one anion of at least one acid and at least one cation of at least one base, wherein the at least one acid is the same in each of the two or more individual separation media and the at least one base is the same in each of the two or more individual separation media.

In a second embodiment of the first aspect which is also an embodiment of the first embodiment of the first aspect, the pH value of the two or more separation media increases from the anode to the cathode.

In a third embodiment of the first aspect which is also an embodiment of the first and the second embodiment of the first aspect, the separation medium comprises 2, 3, 4, 5, 6, 7, 8, 9, 10, 11, 12, 13, 14, 15, 16, 17, 18, 19, 20 or more individual separation media preferably 2 to 10 individual separation media, and more preferably 2 to 7 individual separation media.

In a fourth embodiment of the first aspect which is also an embodiment of the first, second and third embodiment of the first aspect, the separation medium comprises two or more individual separation media, wherein the difference in the pH value between the two or more separation media is a) 1 or less than 1, preferably 0.2 to 0.8; or b) 7 or less than 7, preferably 1.5 to 3.5.

In a fifth embodiment of the first aspect which is also an embodiment of the first, second, third and fourth embodiment of the first aspect, the separation medium comprises three or more individual separation media, wherein the difference in the pH value between the three or more individual separation media is constant.

In a sixth embodiment of the first aspect which is also an embodiment of the first, second, third, fourth and fifth embodiment of the first aspect, the separation medium comprises three or more individual separation media, wherein the difference in the pH value between the three or more individual separation media is not constant.

In a seventh embodiment of the first aspect which is also an embodiment of the first, second, third, fourth, fifth and sixth embodiment of the first aspect, the at least one anion of the at least one acid is the same in each of the two or more individual separation media and the at least one cation of the at least one base is the same in each of the two or more individual separation media.

In an eighth embodiment of the first aspect which is also an embodiment of the seventh embodiment of the first aspect, the pKs value of the acid is from about 3 to 8, preferably from 4 to 7, more preferably from 4 to 6.5 and most preferably from 4 to 5.5.

In a ninth embodiment of the first aspect which is also an embodiment of the seventh and the eighth embodiment of the first aspect, the pKs value of the base is from about 4 to 10, preferably from 5 to 9, more preferably from 5 to 8 and most preferably from 6 to 8.

In a tenth embodiment of the first aspect which is also an embodiment of the seventh, eighth and ninth embodiment of the first aspect, the concentration of the anion in at least one or each of the at least two individual separation media is from about 3-100 mM, preferably 5 to 50 mM, more preferably 10 to 30 mM and most preferably 10 to 20 mM.

In an eleventh embodiment of the first aspect which is also an embodiment of the seventh, eighth, ninth and tenth embodiment of the first aspect, in case of a cationic separation the concentration of the cation in at least one or each of the at least two individual separation media is from 5-50 mM.

In a twelfth embodiment of the first aspect which is also an embodiment of the seventh, eighth, ninth and tenth embodiment of the first aspect, in case of an anionic separation the concentration of the anion in at least one or each of the at least two individual separation media is from 5-50 mM.

In a 13$^{th}$ embodiment of the first aspect which is also an embodiment of the seventh, eighth, ninth, tenth, eleventh and twelfth embodiment of the first aspect, the concentration of the acid is up to 500 mM at the pH of the individual separation medium at the cathode or at the pH of the border stabilization medium at the cathode.

In a 14$^{th}$ embodiment of the first aspect which is also an embodiment of the seventh, eighth, ninth, tenth, eleventh, twelfth and 13$^{th}$ embodiment of the first aspect, the concentration of the base is up to 500 mM at the pH of the individual separation medium at the anode or at the pH of the border stabilization medium at the anode.

In a 15$^{th}$ embodiment of the first aspect which is also an embodiment of the seventh, eighth, ninth, tenth, eleventh, twelfth, 13$^{th}$ and 14$^{th}$ embodiment of the first aspect, the anion bears a single negative charge at the pH value of the individual separation media.

In a 16$^{th}$ embodiment of the first aspect which is also an embodiment of the seventh, eighth, ninth, tenth, eleventh, twelfth, 13$^{th}$, 14$^{th}$ and 15$^{th}$ embodiment of the first aspect, the cation bears a single positive charge at the pH value of the individual separation media.

In a 17$^{th}$ embodiment of the first aspect which is also an embodiment of the seventh, eighth, ninth, tenth, eleventh, twelfth, 13$^{th}$, 14$^{th}$, 15$^{th}$ and 16$^{th}$ embodiment of the first aspect, the analyte of interest has a pI of >7, and wherein the analyte of interest can be separated at an optimum pH range $pH_{opt}$, wherein $pH_{opt}$ is determined as follows:

$$pI-0.6 < pH_{opt} \leq pI.$$

In an 18$^{th}$ embodiment of the first aspect which is also an embodiment of the seventh, eighth, ninth, tenth, eleventh, twelfth, 13$^{th}$, 14$^{th}$, 15$^{th}$ and 16$^{th}$ embodiment of the first aspect, the analyte of interest has a pI of <7, and wherein the analyte of interest can be separated at an optimum pH range $pH_{opt}$, wherein $pH_{opt}$ is determined as follows:

$$pI \leq pH_{opt} < pI+0.6.$$

In a 19$^{th}$ embodiment of the first aspect which is also an embodiment of the seventh, eighth, ninth, tenth, eleventh, twelfth, 13$^{th}$, 14$^{th}$, 15$^{th}$, 16$^{th}$, 17$^{th}$ and 18$^{th}$ embodiment of the first aspect, the acid is selected from the group comprising gluconic acid, hydroxyisobutyric acid, glutamic acid, isobutyric acid, acetic acid, pivalic acid, MES, MOPS and HEPES.

In a 20$^{th}$ embodiment of the first aspect which is also an embodiment of the seventh, eighth, ninth, tenth, eleventh, twelfth, 13$^{th}$, 14$^{th}$, 15$^{th}$, 16$^{th}$, 17$^{th}$, 18$^{th}$ and 19$^{th}$ embodiment of the first aspect, the base is selected from the group comprising pyridinethanol, BISTRIS, 4-(2-hydroxyethyl) morpholine, TEA, TRIS, diethanol, ammediol and bishydroxypropylamine.

In a 21$^{st}$ embodiment of the first aspect which is also an embodiment of the seventh, eighth, ninth, tenth, eleventh, twelfth, 13$^{th}$, 14$^{th}$, 15$^{th}$, 16$^{th}$, 17$^{th}$, 18$^{th}$, 19$^{th}$ and 20$^{th}$ embodiment of the first aspect, the acid and the base form a combination and the combination is selected from the group comprising (a) BISTRIS and HIBA, (b) BISTRIS and glutamic acid, (c) BISTRIS and gluconic acid, (d) TEA and HIBA, (e) TEA and glutamic acid, (f) TRIS and HIBA, (g) TRIS and MES, (h) diethanol and HIBA, (i) ammediol and HIBA, (j) pyridinethanol and HIBA, (k) TEA and HAC, and (l) 4-(2-hydroxyethyl) morpholine and isobutyric acid.

In a 22$^{nd}$ embodiment of the first aspect which is also an embodiment of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$ and 21$^{st}$ embodiment of the first aspect, the free-flow electrophoresis method is interval free-flow electrophoresis method.

In a 23$^{rd}$ embodiment of the first aspect which is also an embodiment of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$ and 21$^{st}$ embodiment of the first aspect, the free-flow electrophoresis method is a continuous free-flow electrophoresis method.

In a 24th embodiment of the first aspect which is also an embodiment of the first, second, third, fourth, fifth, sixth, seventh, eighth, ninth, tenth, eleventh, twelfth, 13th, 14th, 15th, 16th, 17th, 18th, 19th, 20th, 21st, 22nd and 23rd embodiment of the first aspect, the analytes are selected from the group comprising cells, cell compartments, nanobeads, nanodiscs, viruses and any compounds, whereby the compounds are preferably biological and chemical compounds and more preferably charged biological and chemical compounds.

In a 25th embodiment of the first aspect which is also an embodiment of the 24th embodiment of the first aspect, the biological compound is selected from the group comprising peptide, polypeptide, protein, nucleic acid, carbohydrate and lipid.

In a 26th embodiment of the first aspect which is also an embodiment of the 25th embodiment of the first aspect, the protein is an antibody, preferably a monoclonal antibody.

In a 27th embodiment of the first aspect which is also an embodiment of the 24th embodiment of the first aspect, the cells are selected from the group comprising a eukaryotic cell and a prokaryotic cell.

In a 28th embodiment of the first aspect which is also an embodiment of the 24th embodiment of the first aspect, the cell compartments are selected from the group comprising an organelle, a ribosome, a liposome and a nucleus.

In a 29th embodiment of the first aspect which is also an embodiment of the first, second, third, fourth, fifth, sixth, seventh, eighth, ninth, tenth, eleventh, twelfth, 13th, 14th, 15th, 16th 17th, 18th, 19th, 20th, 21st, 22nd, 23rd, 24th, 25th, 26th, 27th and 28th embodiment of the first aspect, the pH value of the two or more individual separation media is set prior to carrying out the free-flow electrophoresis method.

In a 30th embodiment of the first aspect which is also an embodiment of the first, second, third, fourth, fifth, sixth, seventh, eighth, ninth, tenth, eleventh, twelfth, 13th, 14th, 15th, 16th, 17th, 18th, 19th, 20th, 21st, 22nd, 23rd, 24th, 25th, 26th, 27th, 28th and 29th embodiment of the first aspect, each of the two or more individual separation media comprises at least one anion of two or more acids.

In a 31st embodiment of the first aspect which is also an embodiment of the first, second, third, fourth, fifth, sixth, seventh, eighth, ninth, tenth, eleventh, twelfth, 13th, 14th, 15th, 16th, 17th, 18th, 19th, 20th, 21st, 22nd, 23rd, 24th, 25th, 26th, 27th, 28th, 29th and 30th embodiment of the first aspect, each of the two or more individual separation media comprises at least one cation of two more bases.

In a 32nd embodiment of the first aspect which is also an embodiment of the first, second, third, fourth, fifth, sixth, seventh, eighth, ninth, tenth, eleventh, twelfth, 13th, 14th, 15th, 16th, 17th, 18th, 19th, 20th, 21st, 22nd, 23rd, 24th, 25th, 26th, 27th, 28th, 29th, 30th and 31st embodiment of the first aspect, each of the two or more individual separation media comprises at least one anion of two or more acids and at least one cation of two more bases.

In a 33rd embodiment of the first aspect which is also an embodiment of the first, second, third, fourth, fifth, sixth, seventh, eighth, ninth, tenth, eleventh, twelfth, 13th, 14th, 15th, 16th, 17th, 18th, 19th, 20th, 21st, 22nd, 23rd, 24th, 25th, 26th, 27th, 28th, 29th, 30th, 31st and 32nd embodiment of the first aspect, the two or more acids are two or more different acids and/or the two or more bases are two or more different acids.

In a 34th embodiment of the first aspect which is also an embodiment of the first, second, third, fourth, fifth, sixth, seventh, eighth, ninth, tenth, eleventh, twelfth, 13th, 14th, 15th, 16th, 17th, 18th, 19th, 20th, 21st, 22nd, 23rd, 24th, 25th, 26th, 27th, 28th 29th, 30th, 31st 32nd and 33nd embodiment of the first aspect, the two or more acids and/or the two or more bases are the same in each of the two or more individual separation media.

In a 35th embodiment of the first aspect which is also an embodiment of the first, second, third, fourth, fifth, sixth, seventh, eighth, ninth, tenth, eleventh, twelfth, 13th, 14th, 15th, 16th, 17th, 18th, 19th, 20th, 21st, 22nd, 23rd, 24th, 25th, 26th, 27th, 28th, 29th, 30th, 31st, 32nd, 33rd and 34th embodiment of the first aspect, the method is used for analytical purposes.

In a 36th embodiment of the first aspect which is also an embodiment of the first, second, third, fourth, fifth, sixth, seventh, eighth, ninth, tenth, eleventh, twelfth, 13th, 14th, 15th, 16th, 17th, 18th, 19th, 20th, 21st, 22nd, 23rd, 24th, 25th, 26th, 27th, 28th, 29th, 30th, 31st, 32nd, 33rd, 34th and 35th embodiment of the first aspect, the method is used for preparative purposes.

Furthermore, the problems underlying the present invention are solved in a second aspect which is also a first embodiment of the second aspect, by a kit suitable for use in a free-flow electrophoresis method of the present invention in each and any of its embodiments, and particularly in any one of the first, second, third, fourth, fifth, sixth, seventh, eighth, ninth, tenth, eleventh, twelfth, 13th, 14th, 15th, 16th, 17th, 18th, 19th, 20th, 21st, 22nd, 23rd, 24th, 25th, 26th, 27th, 28th, 29th, 30th, 31st, 32nd, 33rd, 34th, 35th and 36th embodiment of the first aspect, wherein the kit comprises at least two or more individual separation media, wherein the at least two or more separation media differ in their pH value and optionally an instruction leaflet.

Furthermore, the problems underlying the present invention are solved in a third aspect which is also a first embodiment of the third aspect, by the use of a device for use in a free-flow electrophoresis method of the present invention in each and any of its embodiments, and particularly in any one of the first, second, third, fourth, fifth, sixth, seventh, eighth, ninth, tenth, eleventh, twelfth, 13th, 14th, 15th, 16th, 17th, 18th, 19th, 20th, 21st, 22nd, 23rd, 24th, 25th 26th, 27th, 28th, 29th, 30th, 31st, 32nd, 33rd, 34th, 35th and 36th embodiment of the first aspect, wherein the device comprises a separation chamber through which a separation medium may flow and which is a space defined by a floor and a cover and spacers separating the floor and the cover, a pump for supplying the separation medium entering the separation chamber via one or more medium feed lines and leaving the chamber via outlets, at least two electrodes for applying an electric field within the separation medium, one more sample injection points for adding an analyte or a mixture of analytes, and fractionation points for removing the analyte, a fractioned analyte, a separated analyte or a fractioned mixture of analytes separated by free-flow electrophoresis in the separation medium.

The present inventors have surprisingly found that by a free-flow electrophoresis method for separating at least one analyte of interest from a mixture of analytes, wherein the method comprises flowing a separation medium through a separation chamber in a flow direction;

applying an electric field in the separation medium by an anode and a cathode, wherein the anode and the cathode are located at a distance from each other and the separation medium flows between the anode and the cathode, and applying the mixture of analytes to the separation medium, whereupon the at least one analyte of interest is separated from the mixture of analytes, or applying the mixture of analytes to the separation medium, and applying an electric field in the separation medium by an anode and a cathode, wherein the anode and the cathode are located at a distance from each other and the separation medium flows between the anode and the cathode, whereupon the at least one analyte of interest is separated from the mixture of analytes;

collecting fractions of the separation medium with at least one fraction comprising the at least one analyte of interest separated from the mixture of analytes;

wherein the separation medium comprises two or more individual separation media, wherein the two or more individual separation media differ in their pH value, wherein preferably each of the two or more individual separation media comprise at least one anion of at least one acid and at least one cation of at least one base, wherein the at least one acid is the same in each of the two or more individual separation media and the at least one base is the same in each of the two or more individual separation media, a broadening of bands and particularly the broadening of bands carrying an analyte of interest or analytes of interest can be avoided or decreased. Because of this, the method of the invention provides for improved separation efficiency. More preferably, in the free-flow electrophoresis method of the invention the two or more individual separation media differ as to the concentration of the anion and/or of the cation contained in the two or more individual separation media. In accordance therewith, the two or more individual separation media differ as to their relative concentration of the at least one anion and/or of the at least one cation contained in the two or more individual separation media. In accordance therewith, preferably in such embodiment, the separation medium comprises at least one anion and at least one cation, wherein the relative concentration of the at least one anion and/or of the least one cation various across the separation medium with each of the two or more individual separation media providing a distinct concentration of the at least one anion and/or of the at least one cation.

It is within the present invention that the acid is a monovalent acid. It is also within the present invention that the acid is a divalent acid or a polyvalent acid. In case the acid is a divalent or polyvalent acid, the individual separation medium and/or the individual separation media may contain two forms of anions of the respective acid (in case of a divalent acid or a polyvalent acid) or three or more forms of anions of the respective acid (in case of a polyvalent acid). It is also within the present invention that the base is a monovalent base. It is also within the present invention that the base is a divalent base or a polyvalent base. In case the base is a divalent or polyvalent base, the individual separation medium and/or the individual separation media may contain two forms of cations of the respective base (in case of a divalent acid or a polyvalent base) or three or more forms of cations of the respective base (in case of a polyvalent base). Preferably, in case the acid is a bivalent or polyvalent acid the ratio of the various anions of such acid will vary between the individual separation media and thus over the entire separation medium. Preferably, in case the base is a bivalent or polyvalent base the ratio of the various cations of such base will vary between the individual separation media and thus over the entire separation medium.

It is within the present invention that each of the two or more individual separation media comprises at least one anion of two or more acids. Accordingly, each of the two or more individual separation media comprises an anion of the first of the two or more acid, an anion of the second of the two or more acids, and so on. Again, if the acid is a bivalent acid or a polyvalent acid, there may be more than one anion of such acid present in the two or more individual separation media. It is within the present invention that each of the two or more individual separation media comprises at least one cation of two or more bases. Accordingly, each of the two or more individual separation media comprises a cation of the first of the two or more bases, a cation of the second of the two or more bases, and so on. Again, if the base is a bivalent base or a polyvalent base, there may be more than one cation of such base present in the two or more individual separation media. The ratio between the first and the second acid (and/or any further acid) contained in each of the individual separation media can be constant over the entirety of the individual separation media and thus over the separation medium, or such ratio can vary over the entirety of the individual separation media and thus over the separation medium.

Such mixtures of acids and bases, particularly if they have similar electrophoretic mobilities, can be used for an efficient separation, preferably of analytes and more preferably of proteins, most preferably where the proteins of a sample show a broad range of pI-values. More specifically, the variation of the ratio of the concentrations of the two or more bases, preferably with similar values of electrophoretic mobility, allows expanding the pH-range into the alkaline region (pI>7). In a similar approach mixtures of two or more acids, preferably with similar values of electrophoretic mobility, can be used to expand the pH-range into the alkaline region (pI<7).

Without wishing to be bound by any theory, the present inventors proved by series of experiments, that by using a separation medium in a free-flow electrophoresis method, whereby the separation medium comprises at least two individual separation media and whereby the at least two individual separation media differ in their pH value, one or several physical and electrochemical effects can be decreased or avoided which would otherwise contribute to a broadening of a band and particularly a broadening of bands carrying an analyte of interest or analytes of interest. Such effects are diffusion, thermal convection, electroendosmosis, broadening of the laminar flow profile and kinetic and/or electrokinetic effects. More specifically, the bandwidth of any analyte, including the analyte of interest, crossing the boundary between the separation media with difference in pH-values will be minimized in an analogous mode as the values of electrophoretic mobility of the analytes will change.

In connection with the present invention the individual separation media form, in their entirety, the separation medium.

It will be acknowledged by a person skilled in the art that in the method of the present invention, preferably, the current or flow of ions across the interfaces between the individual separation media is not interrupted at such interfaces but keeps on flowing across such interfaces, more preferably the flow across such interfaces is essentially the same as within an individual separation medium.

In an embodiment, the analyte of interest is part of or contained in a mixture of analytes, prior to the mixture of analytes being subjected to the free-flow electrophoresis method of the present invention. In the course of such method of the invention, the analyte of interest is separated from the mixture of the analytes. Such separation may result in the mixture of analytes containing no longer the analyte of interest or containing a lower amount of the analyte of interest compared to the mixture of analytes prior to being subjected to the method of the present invention. The mixture of analytes containing no longer the analyte of interest or containing a lower amount of the analyte of interest compared to the mixture of analytes prior to being subjected to the method of the present invention is also referred to as the remainder of the analytes.

In an embodiment, a sample as used herein is a mixture of analytes, prior to the mixture of analytes being subjected to the free-flow electrophoresis method of the present invention.

In an embodiment of the method of the invention a pH step-gradient is formed in the separation medium at the interface between two individual separation media having a different pH value.

In an embodiment of the method of the invention an analyte of interest is the at least one of the analytes separated from the remainder of the analytes.

In an embodiment of the method of the invention an analyte of interest is an at least one of the analytes separated from the remainder of the analytes.

In an embodiment of the method of the invention a medium is a liquid, preferably a solution and more preferably a buffered solution and most preferably a buffered aqueous solution.

In a preferred embodiment of the method of the invention, the individual separation media share the same pair of a base and an acid. In connection therewith it will be acknowledged that the ratio of a base in its dissociated form and in its non-dissociated form as present in an individual separation medium and the ratio of an acid in its dissociated form and in its non-dissociated form as present in an individual separation medium is dependent on the pH value in such individual separation medium. Therefore, as the individual separation media differ as to their pH value, such ratios, i.e. the ratio of the base in its dissociated form and in its non-dissociated form as present in an individual separation medium and the ratio of the acid in its dissociated form and in its non-dissociated form differ among the individual separation media.

In an embodiment, the individual separation media are arranged such that the individual separation medium having the lowest pH value (the most acid one) is the one which is closest to the anode, whereas the individual medium having the highest pH value (the most basic one) is the one which is closest to the cathode. In an embodiment the individual separation media are arranged such within the electric field and the separation chamber, respectively, that a pH gradient is formed by the pH values of the individual separation media with the pH gradient having the lowest pH value at the anode and the highest value at the cathode.

The number of individual separation media, used in this free-flow electrophoresis method of the invention is at least two. It will be acknowledged by a person skilled in the art that, in principle, a higher number of individual separation media will result in better separation efficiency. However, an increase in the number of individual separation media will ultimately be limited by length of the diffusion path of the ions forming the individual separation medium relative to the length of the individual separation medium within the separation medium. Apart from this limitation as to the maximum number of individual separation media forming the separation medium, there may be a limitation arising from handling limitations. Such handling limitations encompass, for example, the provision of channels for introducing the individual separation media into the separation chamber, the preparation of the individual separation media and the like. It will be acknowledged that, in an embodiment, in addition to the individual separation media on one or both sides of the separation medium in flow direction a border stabilization medium is added. The use of a border stabilization medium is described in DE 41 39 472 C1. The border stabilization medium is located between one of the electrodes and the individual separation medium located closest to the electrode. In case the border stabilization medium is located at the anode such stabilization medium is also referred to as the anode border stabilization medium, in case the border stabilization medium is located at the cathode such stabilization medium is also referred to as the cathode border stabilization medium. In an embodiment both an anode border stabilization medium and a cathode border stabilization medium is present.

In an embodiment of the invention, an acid is a proton donor which can be characterized by its pKs value. In an embodiment of the invention, the acid is one having a pKs value from about 3 to 8, preferably from 4 to 7, more preferably from 4 to 6.5 and most preferably from 4 to 5.5.

In a further embodiment, the acid is a monovalent acid.

In an embodiment, the acid is one the solubility of which is up to 500 mM at the pH of the border stabilization medium at the cathode if such border stabilization medium is present. In a further embodiment, the acid is one the concentration of which is up to 500 mM at the pH of the separation medium at or closest to the cathode. In a preferred embodiment, the concentration is about 100 mM.

Examples of this kind of acid which may be used in connection with the invention comprise, but are not limited to saccharin, acetylglycine, salicylic acid, sulfanilic acid, mandelic acid, acetylsalicylic acid (aspirin), gluconic acid, aspartic acid, hydroxyisobutyric acid, benzoic acid, phenylacetic acid, glutamic acid, cinamic acid, vanilic acid, acetic acid, isobutyric acid, nicotinic acid, isonicotinic acid, picolonic acid, sorbic acid, propionic acid, pivalic acid, pyridinethansulfonic acid, diacetylaceton, MES (2-(N-morpholino)ethanesulfonic acid), MOPS (3-(N-Morpholino)-Propansulfonsäure), MOPSO (3-Morpholino-2-hydroxypropanesulfonic acid), ACES (N-(Carbamoylmethyl)-2-aminoethanesulfonic acid), BES (N,N-Bis(2-hydroxyethyl)-2-aminoethanesulfonic acid), MOPS ((3-(N-Morpholino)-Propansulfonsäure), TES (N-[Tris(hydroxymethyl)methyl]-2-aminoethanesulfonic acid), Veronal (5,5-diethylpyrimidine-2,4,6(1H,3H,5H)-trione), HEPES ((4-(2-hydroxyethyl)-1-piperazineethanesulfonic acid)).

In an embodiment of the invention, a base is a proton acceptor which can be characterized by its pKs value. In an embodiment, the base is one having a pKs value from about 4 to 10, preferably from 5 to 9, more preferably from 5 to 8 and most preferably from 6 to 8.

In a further embodiment, the base is a monovalent base.

In an embodiment, the base is one the solubility of which is up to 500 mM at the anode if such border stabilization medium is present. In a further embodiment, the base is one the concentration of which is up to 500 mM at the pH of the separation medium at or closest to the anode. In a preferred embodiment, the concentration is about 100 mM.

Examples of this kind of base which may be used in connection with the invention comprise, but are not limited to creatinin, hydroxymethyl-pyridine, hydroxyethylpyridine, histidine, pyridinethanol, BISTRIS (2-Bis(2-hydroxyethyl)amino-2-(hydroxymethyl)-1,3-propanediol), 4-(2-hydroxyethyl)morpholine, triethanolamine, ethylimidazol, morpholine, TRIS (Tris(hydroxymethyl)aminomethane), diethanolamine, ammediol, benzylamine, phenylethylamine, tri-n-propylamin, triethylamin, bishydroxypropylamine.

In an embodiment of the invention the acid and the base are selected such that the following equation is realized:

$$pKs\ (base)-pKs\ (acid)>n$$

with n being equal to or greater than 1, preferably n being equal to or greater than 2. In an embodiment n is 7 or less. In a further embodiment, n is defined as follows: $1 \leq n \leq 7$, preferably $2 \leq n \leq 7$.

In an embodiment, the pH-range which can be established by the two or more individual separation media and which is therefore established over the separation medium can be defined as follows.

$$pKs\ (acid)-1<pH<pKs\ (base)+1$$

In an embodiment the following combinations of a base and an acid are used so as to establish the following pH ranges over the separation medium:
- pH range from about 4.2 to 7: BISTRIS and HIBA (hydroxyiso-butyric acid); BISTRIS and glutamic acid; or BISTRIS and gluconic acid;
- pH range from about 4 to 8: TEA (triethanol amine) and HIBA; or TEA and glutamic acid;
- pH range from about 6 to 9: TRIS and HIBA; or TRIS and MES;
- pH range from about 6 to 9: diethanol amine and HIBA;
- pH range from about 7 to 9.5: ammediol and HIBA;
- pH range from about 4 to 6: pyridinethanol and HIBA;
- pH range from about 5 to 8: TEA and HAC (acetic acid); and
- pH range from 4.5 to 7.5 4-(2-hydroxyethyl)morpholine and isobutyric acid.

In an embodiment, the difference in pH value between the individual separation media is constant over the entire separation medium. In other words, the difference in pH value between the first individual separation medium and the second individual separation medium is equal or similar to the difference in pH value between the second individual separation medium and the third individual separation medium etc. This embodiment is particularly advantageous in case more than one, preferably several analytes of interest are to be separated.

In an alternative embodiment, the difference in pH value between the individual separation media is not constant over the entire separation medium. For example, the difference in pH value between the first individual separation medium and the second individual separation medium is x1 and the difference in pH value between the second individual separation medium and the third individual separation medium is x2 with x1 being different from x2. Such change in difference in pH value can be constant or can vary.

In connection with each and any embodiment of the various aspects of the present invention it is to be acknowledged that the pH value of the two or more individual separation media is preferably set prior to carrying out the free-flow electrophoresis method; in other words, at least the initial pH value of the two or more individual separation media is not established in the course of carrying out the free-flow electrophoresis method of the invention.

It will be acknowledged by a person skilled in the art that the number of the individual separation media of the separation medium as well as the difference in pH value depend on the sample, the analyte of interest, and the accessory compounds, contained in the sample apart from the analyte of interest, whereby such accessory compounds are preferably the analytes contained in the mixture of analytes different from the analyte of interest. Preferably, the analyte of interest and the accessory compounds contained in the sample form the analytes as subject to the method of the invention. One important factor in connection therewith is the isoelectric point, pI, of the analyte of interest and of the accessory compounds, whereby particularly the difference of the pI of the analyte of interest and some or all of the accessory compounds or particles is crucial. A further factor which is of importance in so far, is the purity of the sample. Such purity of the sample defines the heterogeneity of the compounds or particles contained in the sample. The basic rule in accordance with the method of the invention, particularly in case the concentration of the accessory compounds is significantly higher than the concentration of the analyte of interest, is that the less heterogeneous the sample is, the more fine-tuned the difference in pH can be realized between the individual separation media, and the more accurate the separation of the analyte of interest from the other components of the sample such as, e.g., accessory compounds will be. The same is also true in case the accessory compounds are particles.

In an embodiment the accessory compounds are contaminants.

In an embodiment the difference in pH value between two individual separation media is 1 or less than 1. Preferably the difference in pH value is 0.8 to 0.2. More preferably, the difference in pH value between two individual separation media is 0.2 or 0.1.

In an alternative embodiment the difference in pH value between two individual separation media is 7 or less than 7. Preferably the difference in pH value is 1.5 to 3.5.

In accordance with the above, in an embodiment the difference in pH value between the individual separation media is equal to or greater than 1 in case the primary intention of the method of the invention is to remove accessory compounds or accessory particles. The difference in pH value between the individual separation media is, in an embodiment, equal to or less than 0.5 in case the primary intention of the method of the invention is to finely resolve the components of the sample, preferably separating those accessory compounds of the sample from the analyte of interest which have a pI close to the pI of the analyte of interest.

The method of the invention can be used for anionic separation, for cationic separation and for a combined or simultaneous cationic and anionic separation.

As preferably used herein, an anionic separation is a separation making use of the method of the invention where the analyte of interest migrates under the influence of the applied electric field to the anode.

As preferably used herein, a cationic separation is a separation making use of the method of the invention where the analyte of interest migrates under the influence of the applied electric field to the cathode.

As preferably used herein, a combined or simultaneous cationic and anionic separation is a separation making use of the method of the invention where any anionic analyte of interest migrates under the influence of the applied electric field to the anode, whereas any cationic analyte of interest migrates under the influence of the applied electric field to the cathode.

In an embodiment, the pH value of the individual separation medium within which the analyte of interest is to be maintained, which is also referred to as $pH_{opt}$, is calculated based on the pI of the analyte of interest.

If, in an embodiment, the analyte of interest has an overall positive charge expressed by a pI of >7 such analyte of interest will migrate in separation media of pH<7 to the cathode in a free-flow electrophoresis method, including the free-flow electrophoresis method of the present invention. In this embodiment it is preferred that $pH_{opt}$ is calculated as follows:

$$pI-0.6<pH_{opt}\leq pI$$

If, in an embodiment, the analyte of interest has an overall negative charge expressed by a pI of <7 such analyte of interest will migrate in separation media of pH>7 to the anode in a free-flow electrophoresis method. In this embodiment it is preferred that $pH_{opt}$ is calculated as follows:

$$pI\leq pH_{opt}<pI+0.6$$

It will be acknowledged by a person skilled in the art that the major part of the conductivity of the separation medium is provided by the anions and cations of the base and the acid of the separation medium and the individual separation media, respectively. In an embodiment, the concentration of the anion as provided by the base and acid, respectively, of an individual separation medium is from about 3-100 mM, preferably 5 to 50 mM, more preferably 10 to 30 mM and most preferably 10 to 20 mM. In an embodiment, the concentration of the anion as provided by the base and acid, respectively, of the separation medium is from about 3-100 mM; preferably 5 to 50 mM, more preferably 10 to 30 mM and most preferably 10 to 20 mM.

In an embodiment the ratio of concentration of the acid to concentration of the base, i.e. $[c_{acid}/c_{base}]$, is $$0.1\leq [c_{acid}/c_{base}]\leq 10,$$

preferably $0.25\leq [c_{acid}/c_{base}]\leq 4$.

In an embodiment, the individual separation media exhibit some degree of conductivity. Such conductivity arises from the presence of ions in the individual separation medium, the separation medium and the sample. In addition, ions from other liquids contained or added to the separation chamber such as the border stabilization medium or the dosing medium may contribute to such conductivity. It will, however, be acknowledged by a person skilled in the art that it is preferred not to add any further ions in addition to those which are already contained in the separation media, dosage medium and the border stabilization media. In a further embodiment, additional ions contained in the sample containing the analyte are removed from the sample, preferably in case such additional ions are not compatible with the carrying out of the method of the invention or are decreasing the performance of the method of the invention.

It is preferred that in the practicing of the method of the invention conductivity of the individual separation media is essentially the same. As preferably used herein, conductivity which is essentially the same is one which does not change the electric field in a way which would change the separation efficiency of the method compared to the separation efficiency of the method obtained without the change in conductivity. As alternatively or additionally preferably used herein, conductivity which is essentially the same is a conductivity which differs by less than 10%, preferably less than 5% among the individual separation media forming the separation medium. Such essentially same conductivity is achieved by the selection of a suitable pair of base and acid taking into consideration of pKs values of the base and the acid. In connection therewith the difference between the pKs of the base and the pKs of the base ($\Delta$pKs) is preferably $\geq 2$.

In an embodiment of the method of the invention, a border stabilization medium as used in the method of the invention is of high conductivity. The conductivity of the border stabilization medium is higher than the conductivity of the individual separation media and higher than the conductivity of the separation medium. Conductivity of the border stabilization medium is increased by a factor of $\geq 3$. Preferably, the conductivity of the border stabilization medium $F_{ideal}$ is as follows:

$$10\times F_{sep\ med}<F_{ideal}<50\times F_{sep\ med}$$

with $F_{sep\ med}$ being the conductivity of the individual separation media.

The function of such increase in conductivity of the border stabilization medium relative to the conductivity of the individual separation media is to prevent the analyte(s) from migrating and particularly from diffusing all the way to an electrode. Insofar, the border stabilization medium forms a fluid boundary. In an embodiment the border stabilization medium flows in the same direction as the individual separation media and thus, preferably, the separation medium. In a further embodiment, the border stabilization medium at the anode corresponds in terms of its chemical composition to the chemical composition of the individual separation medium being adjacent to the border stabilization medium at the anode, i.e. the individual separation medium closest to the anode, except that the concentration of the base is increased, preferably by a factor of at least 5, relative to the concentration of the base in said adjacent individual separation medium and, more preferably, that the acid contained in the border stabilization medium is different from the acid of the individual separation media. In a further embodiment, the border stabilization medium at the cathode corresponds in terms of its chemical composition to the chemical composition of the individual separation medium being adjacent to the border stabilization medium at the cathode, i.e. the individual separation medium closest to the cathode, except that the concentration of the acid is increased, preferably by a factor of at least 5, relative to the concentration of the acid in said adjacent individual separation medium and, more preferably, that the base contained in the border stabilization medium is different from the base of the individual separation media.

In an embodiment of the invention, a stabilization medium comprises the at least one anion of at least one acid and/or the at least one cation of at least one base as contained in the separation medium and, preferably, in each of the individual separation media.

In an embodiment of the invention the border stabilization medium at the cathode comprises the at least one anion of the at least one acid as contained in the separation medium and, preferably, in each of the individual separation media.

In an embodiment of the invention the border stabilization medium at the anode comprises the at least one cation of the at least one base acid as contained in the separation medium and, preferably, in each of the individual separation media.

In a further embodiment a border stabilization medium is added to the separation chamber through a separate port, inlet or feeding line.

In an embodiment of the invention dosing medium is used for applying the analytes to the separation medium, and, respectively, to one of the individual separation media. Preferably, the chemical composition of the dosing medium, as to the base and the acid in particular, essentially corresponds to the chemical composition of the individual separation medium into which the sample will be introduced first upon administration to the separation chamber. Additionally, the dosing medium contains 3-20 mM MeCl or MeCl$_2$ with Me being a monovalent or divalent metal ion; preferably the metal ion is selected from the group comprising Na$^+$, K$^+$, Mg$^{2+}$.

In an embodiment of method of the invention, a counterflow medium is used as described in DE 41 39 472. Such counterflow medium is preferably introduced into the separation chamber at or close to the end of the separation chamber where the separation medium leaves the separation medium at or close to the outlets of the separation chamber. In an embodiment the counterflow medium is added in front of, at or after fractionation points for removing the analyte of interest. The flow direction of the counterflow medium is opposite to the flow direction of the separation medium. It will be appreciated by the person skilled in the art that, preferably, the counterflow medium will be selected, to have a low value of conductivity and this medium will preferably contain a concentration up to 100 mM of a pair of acid and base whose pKs-values will follow the general rule below:

2<pKs (acid)−pKs (base)<3

In an embodiment the method of the invention can be used for performing an anionic separation. In such embodiment, a sample containing a mixture of analytes is applied to the individual separation medium having the highest pH value of the individual separation media forming the separation medium. In a further embodiment the method of the invention can be used for performing a cationic separation. In such embodiment, the sample containing a mixture of analytes is applied to the individual separation medium having the lowest pH value of the individual separation media forming the separation medium. The application of the sample to the individual separation medium having the highest pH value and, respectively, having the lowest pH value ensures that a maximum separation path is used by the analyte of interest contained in the sample and exposure time of the analyte of interest contained in the sample to the electric field is maximum which increases separation efficiency with the separation efficiency being defined as the product of the strength of the applied electric field and time.

In an embodiment of the method of the invention the free-flow electrophoresis method is an interval free-flow electrophoresis method. The principle of interval free-flow electrophoresis and how to apply it is described in DE 197 11 898 A1. Basically, a laminar flow profile is generated by the liquid separation medium passing through a separation chamber and more specifically passing through the gap between plates forming the separation chamber. The characteristics of the laminar flow profile depend on several factors such as the width of the gap and the viscosity of the separation medium. In contrast to continuous free-flow electrophoresis, the analytes are exposed to the electric field for the same period of time in interval free-flow electrophoresis. This results in a more accurate separation of the analytes and thus in more focused bands for the individual analytes after separation and hence an increase in separation efficiency.

The analyte separated by performing FFE can be used for analytic purposes or for further preparative processing. Accordingly, FFE can be used for analytical or preparative purposes and, therefore, at an analytical or a preparatory scale.

In a further aspect the present invention is related to a kit. The kit of the invention is suitable for use in the performing of the method of the invention and contains at least two individual separation media as described in connection with the method of the invention. In an embodiment the kit of the invention additionally comprises at least one of a border separation medium as disclosed in connection with the method of the invention, an electrode suitable for use in the method of the invention, a device suitable for performing the method of the invention and an instruction leaflet.

It will be acknowledged that any feature disclosed in connection with the method of the invention and in connection with the separation medium and the individual separation media and the border separation media in particular, is also a feature of the kit of the invention, at least to the extent that the kit contains such separation medium and the individual separation media and the border separation media.

In a still further aspect the present invention is related to the use of a device suitable for performing a free-flow electrophoresis device. Such device is, for example, described in any of DE 41 39 472 C1, DE 197 11 898 A1, U.S. Pat. No. 7,169,275 B2, U.S. Pat. No. 7,169,278 B2 or WO 02/50524.

In accordance therewith, the device of the invention comprises a separation chamber through which a separation medium may flow and which is a space defined by a floor and a cover and spacers separating the floor and the cover, a pump for supplying the separation medium entering the separation chamber via one or more medium feed lines and leaving the chamber via outlets, at least two electrodes for applying an electric field within the separation medium, one or more sample injection points for adding a sample, an analyte of interest, or a mixture of analytes, and fractionation points for removing the analyte of interest, a fractioned analyte, a separated analyte, a fractioned mixture of analytes or the remainder of the analytes separated by free-flow electrophoresis in the separation medium. In a preferred embodiment the device comprises one pump for supplying the separation medium, nine medium feed lines, five injection points, 96 fractionation points and 96 outlets.

BRIEF DESCRIPTION OF THE DRAWINGS

The present invention will now be further illustrated by the following drawings and examples, from which further features, embodiments and advantages of the invention may be taken, whereby.

DESCRIPTION OF PREFERRED EMBODIMENTS

Figure 1:
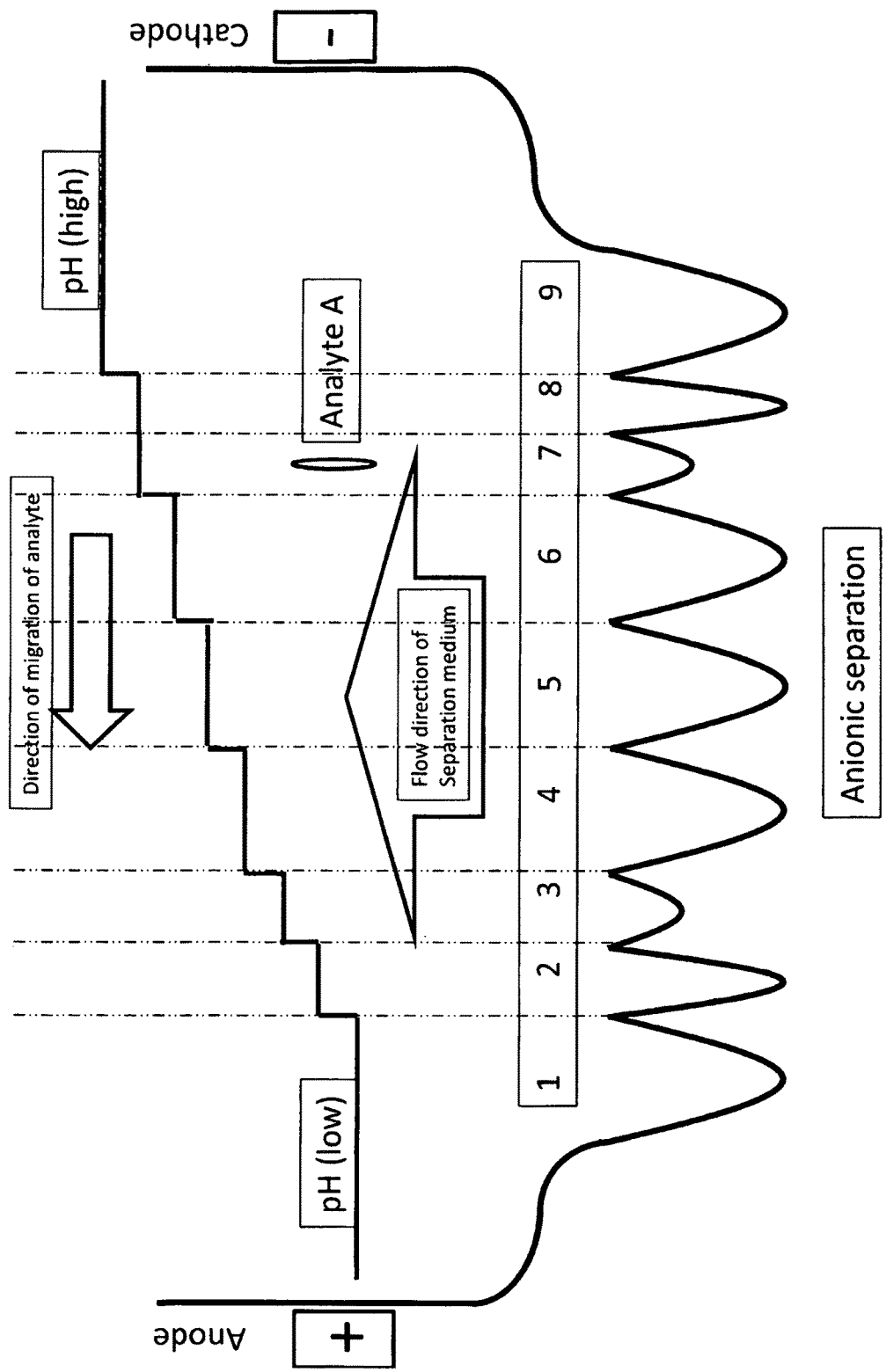
FIG. 1 is an illustration of an embodiment of the method of the invention where the analyte of interest is an anion and the method thus provides an anionic separation.

FIG. 1 is an illustration of an embodiment of the method of the invention. In the embodiment shown the separation is an anionic separation. In such anionic separation the analyte of interest is an anion. Separation medium S consists of individual separation media 2, 3, 4, 5, 6, 7 and 8 which differ in their pH value. Due to such difference in pH value a step-gradient is formed over separation medium S. Separation medium S is flanked on the side of the cathode by border stabilization medium 9 and on the side of the anode by border stabilization medium 1. Both border stabilization medium 1 and border stabilization medium 9 have a conductivity which is increased compared to conductivity of individual separation media 2, 3, 4, 5, 6, 7 and 8. As the analyte of interest is an anion Analyte A which is a mixture of analytes or a sample, is applied to individual separation medium 7 which is closer to the cathode than to the anode (+) and thus to an individual separation medium having a comparatively higher pH value than most of the other individual separation media. Under the influence of the electric field the analyte of interest contained in Analyte A which is a mixture of analytes or a sample, being moved along the direction of the separation medium will be separated from the remaining analytes. As the analyte of interest is an anion it will move to the anode as indicated in FIG. 1 by the arrow "direction of migration of analyte".

Figure 2:
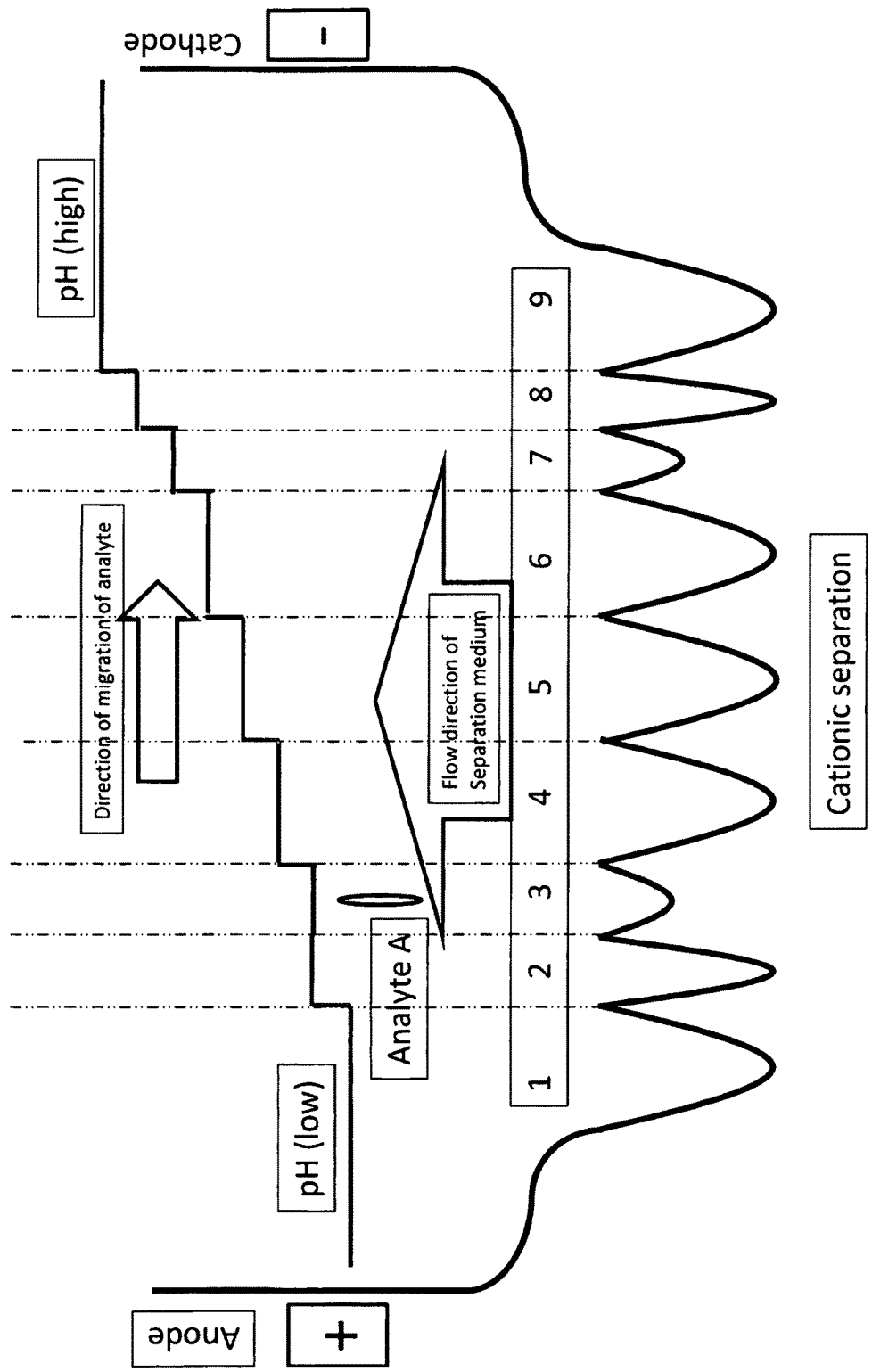
FIG. 2 is an illustration of an embodiment of the method of the invention where the analyte of interest is a cation and the method thus provides a cationic separation.

FIG. 2 is an illustration of a further embodiment of the method of the invention. In the embodiment shown the separation is a cationic separation. In such separation the analyte of interest is a cation. As the analyte of interest is a cation Analyte A which is a mixture of analytes or a sample, is applied to individual separation medium 3 which is closer to the anode (+) than to the cathode (−) and thus to an individual separation medium having a comparatively lower pH value than most of the other individual separation media. Under the influence of the electrical field the analyte of interest contained in Analyte A being moved along the direction of the separation medium will be separated from the remaining analytes. As the analyte of interest is a cation it will move to the cathode as indicated in FIG. 2 by the arrow "direction of migration of analyte". Otherwise, the method is similar to the one described in connection with FIG. 1.

Figure 3:
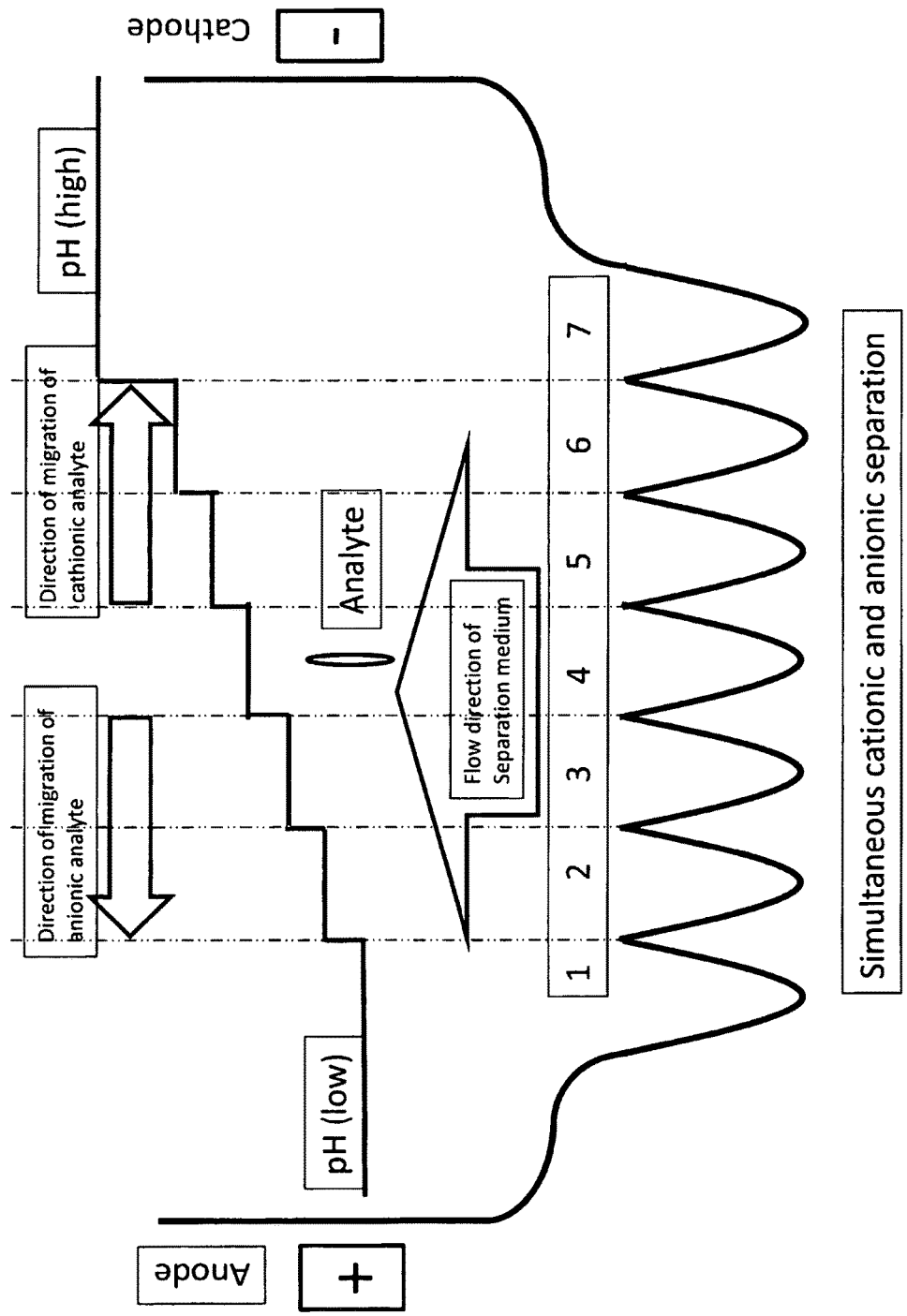
FIG. 3 is an illustration of an embodiment of the method of the invention where the analyte comprises an analyte of interest which is a cation and an analyte of interest which is an anion, and the method is thus a simultaneous anionic separation and a cationic separation.

FIG. 3 is an illustration of a still further embodiment of the method of the invention. In the embodiment shown the separation is a simultaneous cationic separation and anionic separation. Separation medium S consists of individual separation media 2, 3, 4, 5, and 6 which differ in their pH value. Due to such difference in pH value a step-gradient is formed over separation medium S. Separation medium S is flanked on the side of the cathode by border stabilization medium 7 and on the side of the anode by border stabilization medium 1. Both border stabilization medium 1 and border stabilization medium 7 have a conductivity which is increased compared to conductivity of individual separation media. In such separation the analyte comprises an analyte of interest which is a cation and an analyte of interest which is an anion. Because of this, Analyte A which is a mixture of analytes or a sample, is applied to individual separation medium 4 which is about equally distant from both the cathode and the anode and thus to an individual separation medium having a pH value which is in the middle of the pH values defined by the individual separation media 2 and 6. Under the influence of the electrical field the analyte of interest contained in Analyte A being moved along the direction of the separation medium will be separated from the remaining analytes. The cationic analyte of interest being a cation will move to the cathode as indicated in FIG. 3 by the arrow "direction of migration of cationic analyte", whereas the anionic analyte of interest being an anion will move to the anode as indicated in FIG. 3 by the arrow "direction of migration of anionic analyte". Otherwise, the method is similar to the one described in connection with FIGS. 1 and 2.

Figure 4:
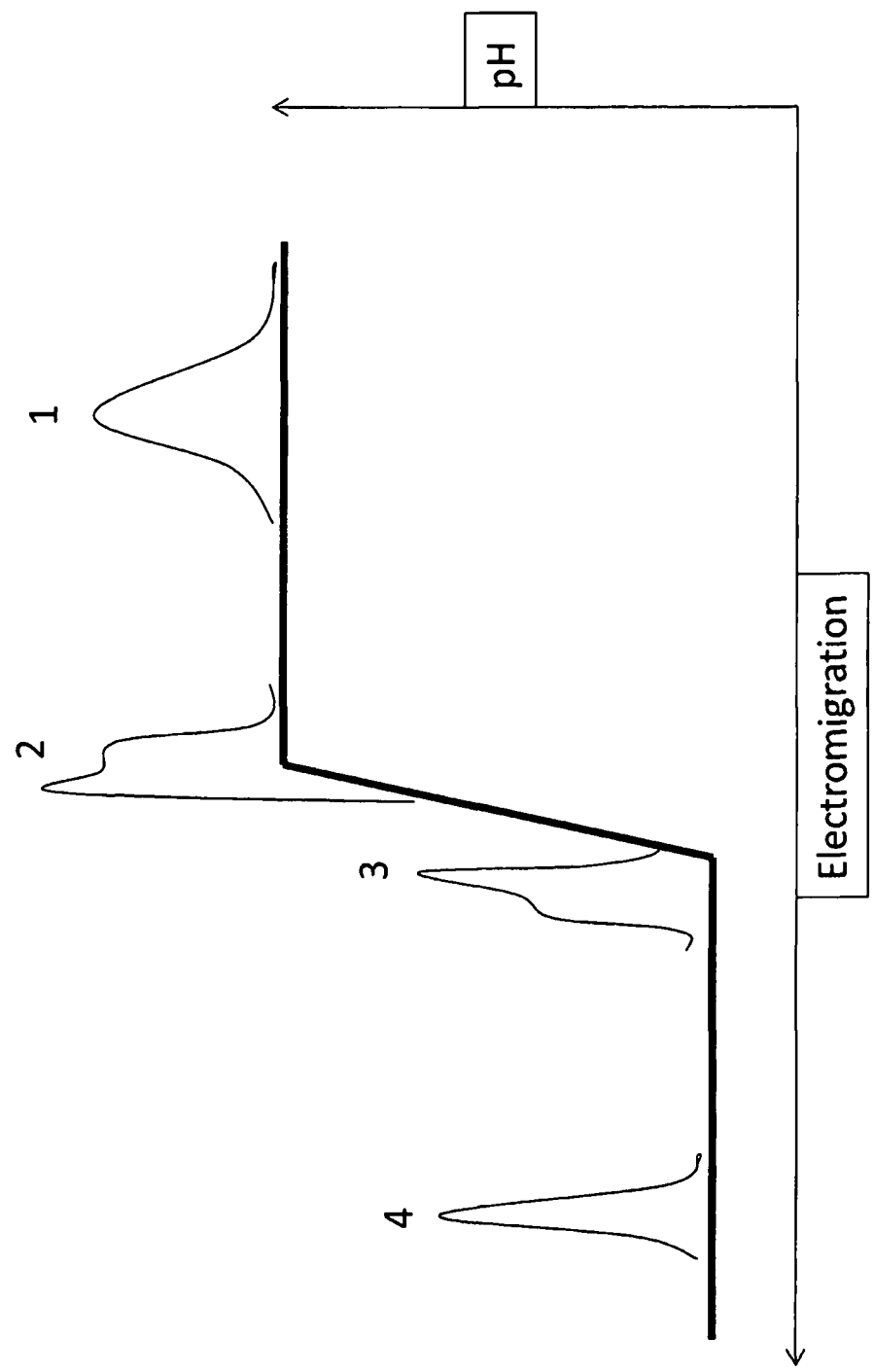
FIG. 4 is an illustration of the effect arising from pH step-gradients on separation efficiency and a sharpening of the analyte bands.

FIG. 4 is an illustration of the effect arising from a pH step-gradient on separation efficiency. More specifically, FIG. 4 shows the different band widths of any anionic amphoteric analyte of interest at the interface of individual separation media having different pH values. Band width decreases and the concentration of the analyte increases in the maximum of the band due to a significant decrease in electrophoretic migration of the analyte when passing from one individual separation medium to another individual separation medium. This kind of advantageous effect can be observed irrespective of whether the method of the invention is carried out as an interval free flow electrophoresis or as a continuous free flow electrophoresis.

Figure 11:
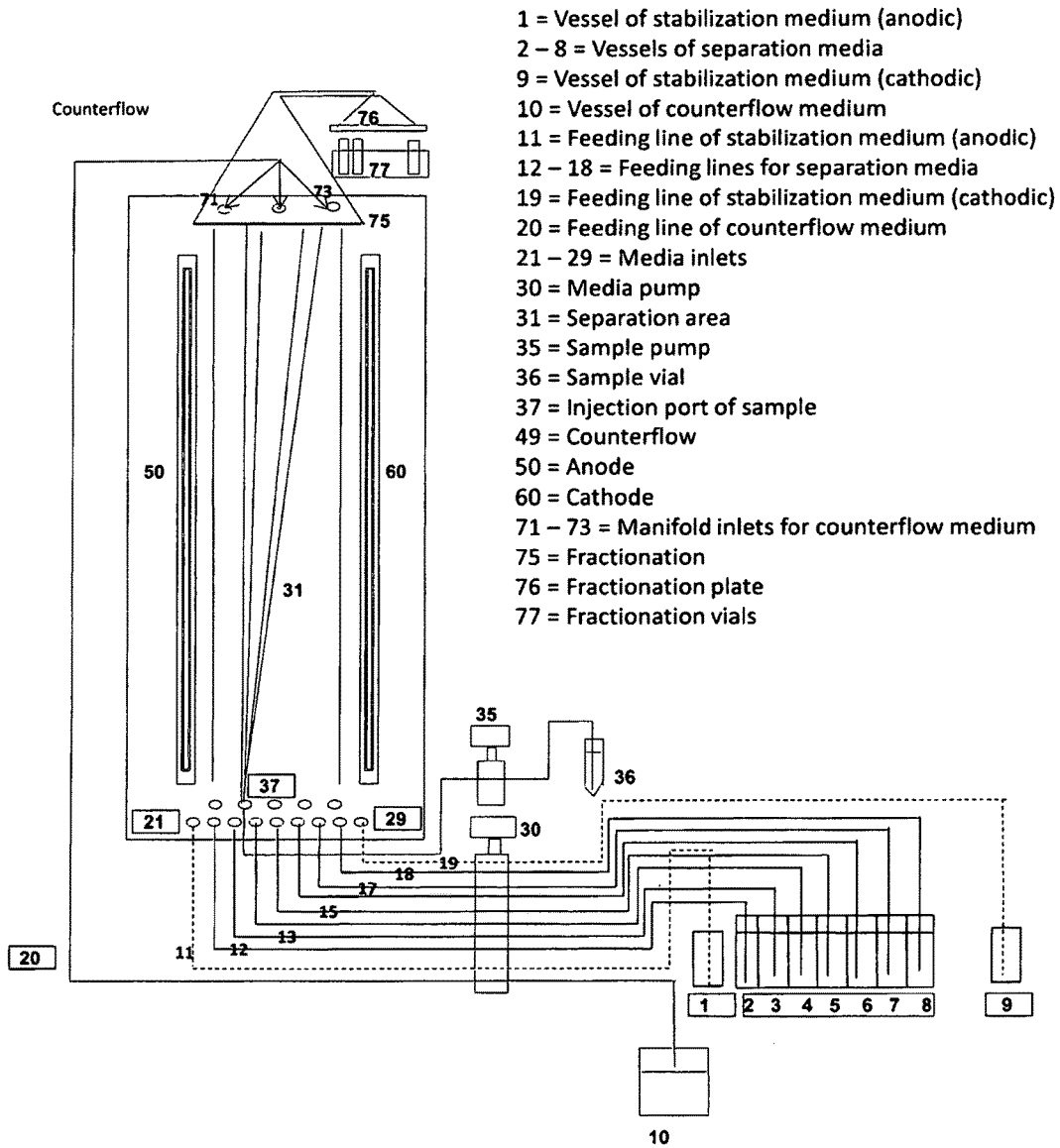
FIG. 11 is an illustration of a device of the invention for free-flow electrophoresis used in the performing of the method of the invention.

FIG. 11 is an illustration of a device for free-flow electrophoresis used in performing the method of the invention. The individual separation media inside the vessels 2 to 8 are supplied by means of pump 30 and the media feeding lines 12 to 18 to the media inlets 22 till 28.

Additionally, two border stabilization media inside the vessels 1 and 9 are transported by pump 30 via the feeding lines 11 and 19 and via the media inlets 21 and 29 into the separation medium 31, which functions as the separation area, in the neighborhood of the anode 50 and cathode 60. Furthermore, a counterflow medium is supplied by pump 30 from vessel 10 via the feeding line 20 to the manifold inlets 71, 72 and 73 and will enter to the fractionation area 75.

Analytes are supplied from sample container 36 by means of pump 35 to injection port 37. The thus applied analytes are transported along the flow direction of the separation medium formed by individual separation media 8 to fractionation area 75 comprising fractionation plate 76 with fractionation vials 77. At fraction area 75 individual fractions of the separation medium are collected. The Fig. describes the migration path of two different analytes, if the separation process will be operated as a continuous free-flow electrophoresis method. Voltage is applied to the anode 50 and cathode 60 for the entire period of time while the analyte migrates along the separation area. If operated so as to realize an interval free-flow electrophoresis, voltage is applied to the anode and cathode only for a certain period of time during the migration of the analyte along the separation medium. The migration path of the analytes will look like 2 parallel zones of migration.

Example 1: Separation of Analytes Consisting of a Mixture of Amphoteric Dyes and Non-Amphoteric Dye SPADNS Analytes consisting of a mixture of amphoteric dyes and non-amphoteric dye SPADNS were subject to the method of the invention realizing a pH step-gradient, whereby the method was carried out as an interval free-flow electrophoresis method (see FIG. 5). In order to show the advantage of the method of the invention, the same experiment was carried out using the same method of FF-Interval-zone electrophoresis except that no pH gradient was realized (see FIG. 6).

The experimental details of the experiments underlying FIGS. 5 and 6 were as follows.

The separation was conducted in a FFE system on a 0.2 mm gap.

The individual separation media and border stabilization media were as follows:

| | |
|---|---|
| Anode border stabilization medium: (inlet 1) | 150 mM HCl<br>300 BISTRIS<br>250 mM Mannitol |
| Individual separation medium 1: (inlet 2&3) | 10 mM BISTRIS<br>adjusted to pH 4.77 with glutamic acid<br>250 mM Mannitol |
| Individual separation medium 2: (inlet 4) | 10 mM glutamic acid<br>adjusted to pH 5.81 with BISTRIS<br>250 mM Mannitol |
| Individual separation medium 3: (inlet 5) | 10 mM glutamic acid<br>adjusted to pH 6.08 with BISTRIS<br>250 mM Mannitol |
| Individual separation medium 4: (inlet 6-8) | 10 mM glutamic acid<br>adjusted to pH 6.87 with BISTRIS<br>250 mM Mannitol |
| Cathode border stabilization medium: | 200 mM triethylamine<br>100 mM EtOH amine<br>50 mM TEA<br>200 mM glutamic acid<br>250 mM Mannitol |
| Counterflow medium: | 250 mM Mannitol |

The sample was injected at individual separation medium 5 with 2000 µl/h; separation was conducted at 1200V and 53 mA on a 4.5 Minute interval at a media speed of ~40 ml/h. FIG. 6:

The separation was conducted in a FFE system on a 0.2 mm gap.

The individual separation medium and border stabilization media were as follows:

| | |
|---|---|
| Anode border stabilization medium: (inlet 1) | 150 mM HCl<br>300 BISTRIS<br>250 mM Mannitol |
| Individual separation medium 1: (inlets 2-5) | 10 mM glutamic acid<br>250 mM Mannitol<br>adjusted to pH 6.86 with BISTRIS |
| Separation buffer 2: (inlets 6-8) | 10 mM glutamic acid<br>250 mM Mannitol<br>adjusted to pH 6.87 with BISTRIS |
| Cathode border stabilization medium: | 200 mM triethylamine<br>100 mM EtOH amine<br>50 mM TEA<br>200 mM glutamic acid<br>250 mM Mannitol |
| Counterflow medium: | 250 mM Mannitol |

The sample was injected at individual separation medium 5 with 2000 µl/h; separation was conducted at 1200V and 53 mA on a 4.5 Minute interval at a media speed of ~40 ml/h.

Figure 5:
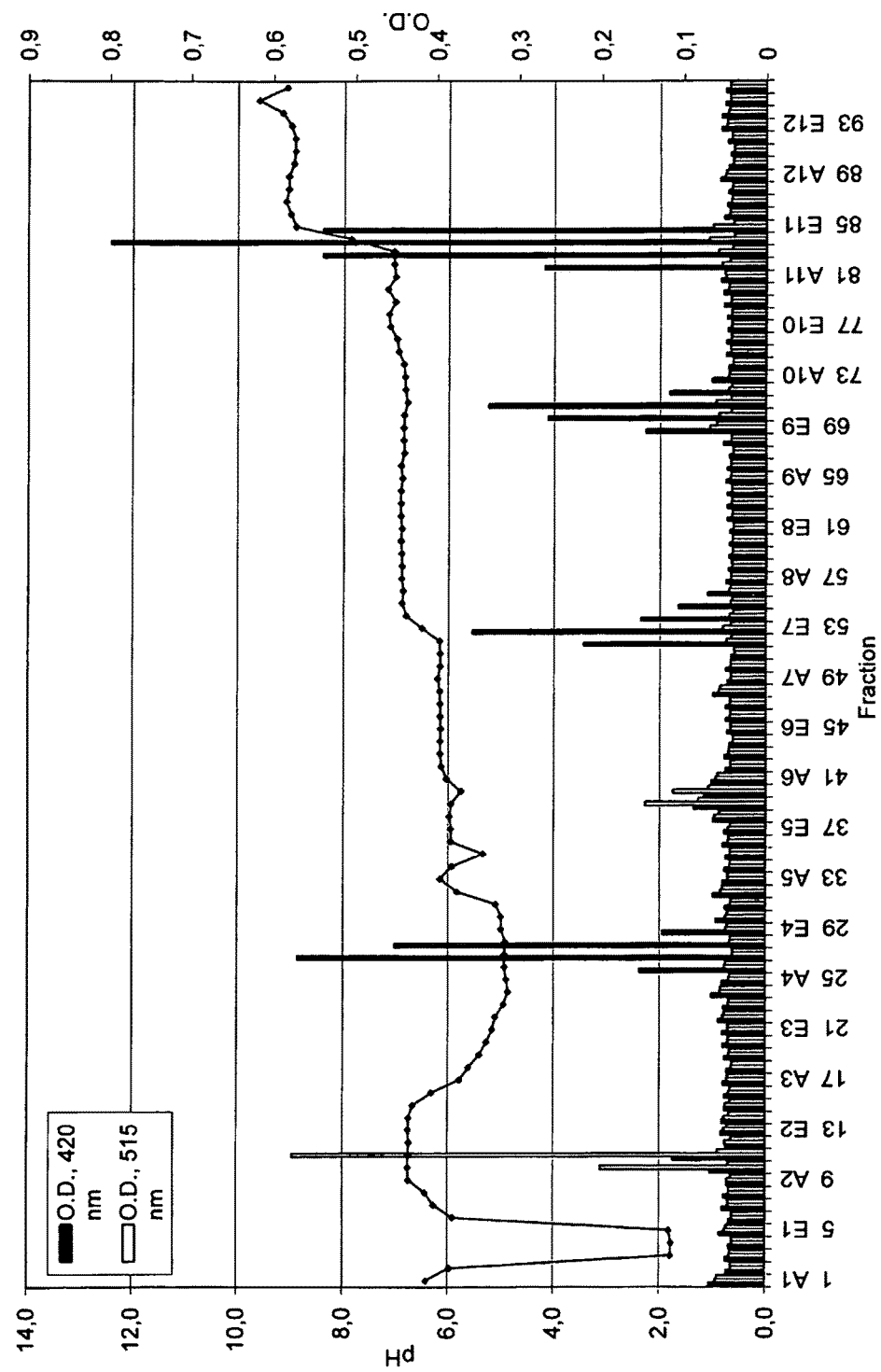
FIG. 5 is a diagram illustrating the result of separating an analyte consisting of a mixture of amphoteric dyes and non-amphoteric dye SPADNS (Trisodium 2-(4-sulfophenylazo)-1,8-dihydroxynaphthalene-3,6-disulfonate) using the method of the invention realizing a pH step-gradient, whereby the method was carried out as an interval free-flow electrophoresis method. The X-axis indicates the fractions obtained at the fraction points, the Y-axis on the left side indicates the pH value measured in the individual fractions (depicted as full diamonds), and the Y-axis on the right side indicates optical density measured at 420 nm (depicted as full columns)
Figure 6:
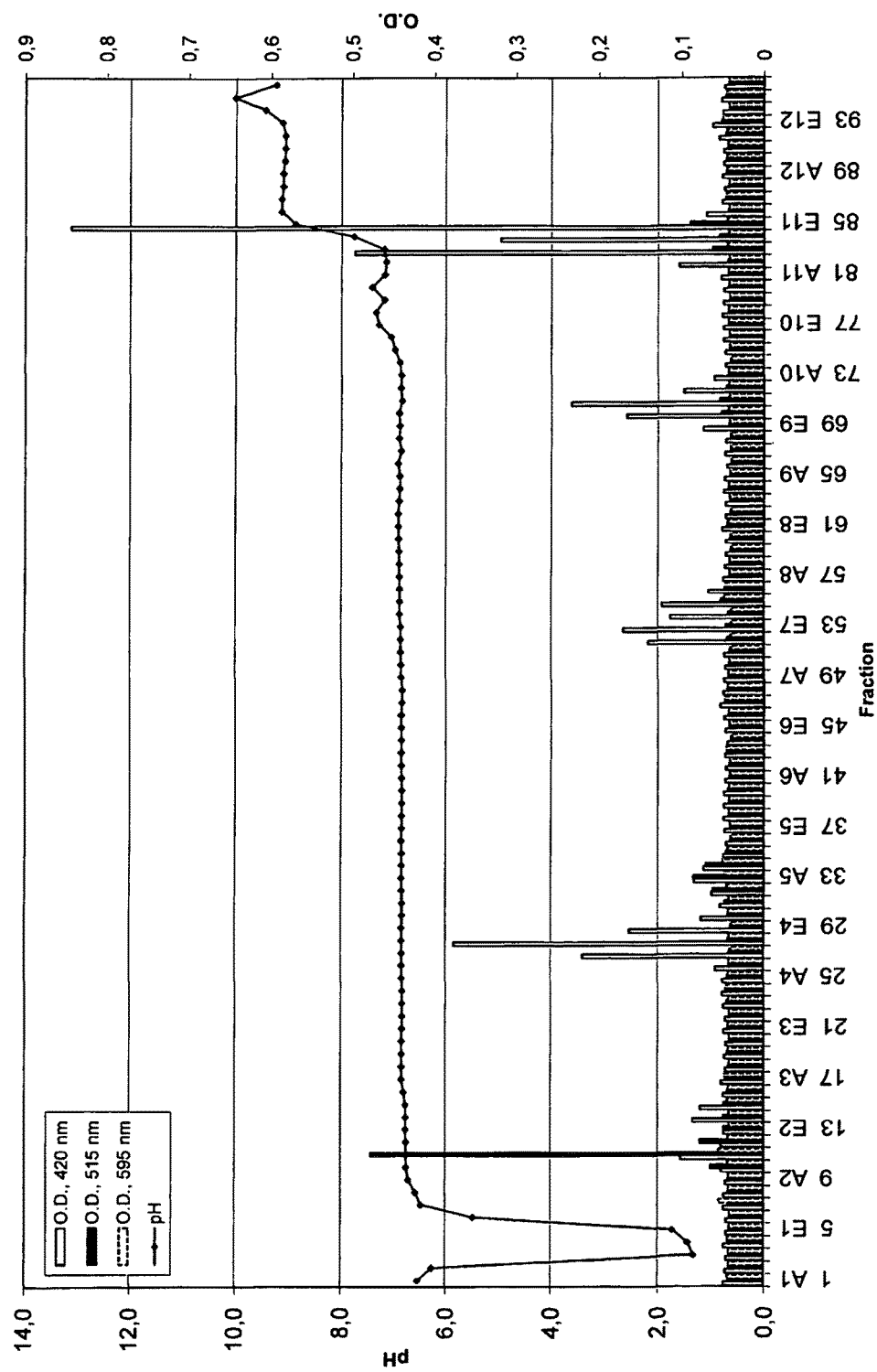
FIG. 6 is a diagram illustrating the result of separating an analyte of interest, namely non-amphoteric dye SPADNS (trisodium 2-(4-sulfophenylazo)-1,8-dihydroxynaphthalene-3,6-disulfonate), from a mixture consisting of a mixture of amphoteric dyes and said non-amphoteric dye SPADNS using a free-flow electrophoresis method of the prior art realizing a constant pH value across the separation medium, whereby the method was carried out as an interval free-flow electrophoresis method. The X-axis indicates the fractions obtained at the fraction points, the Y-axis on the left side indicates the pH value measured in the individual fractions (depicted as full diamonds), and the Y-axis on the right side indicates optical density measured at 420 nm (depicted as full columns)

The results are shown in FIGS. 5 and 6. FIGS. 5 and 6 display the profile of pH-values and the concentration profiles of the separated analytes inside the sample. In case of the process being FF-interval zone electrophoresis, the use of separation media with pH-gradients will give the surplus of quality of separation of the target analytes (pI 4.0, pI 4.75 and pI 5.3), marked inside the graphs.

Figure 7:
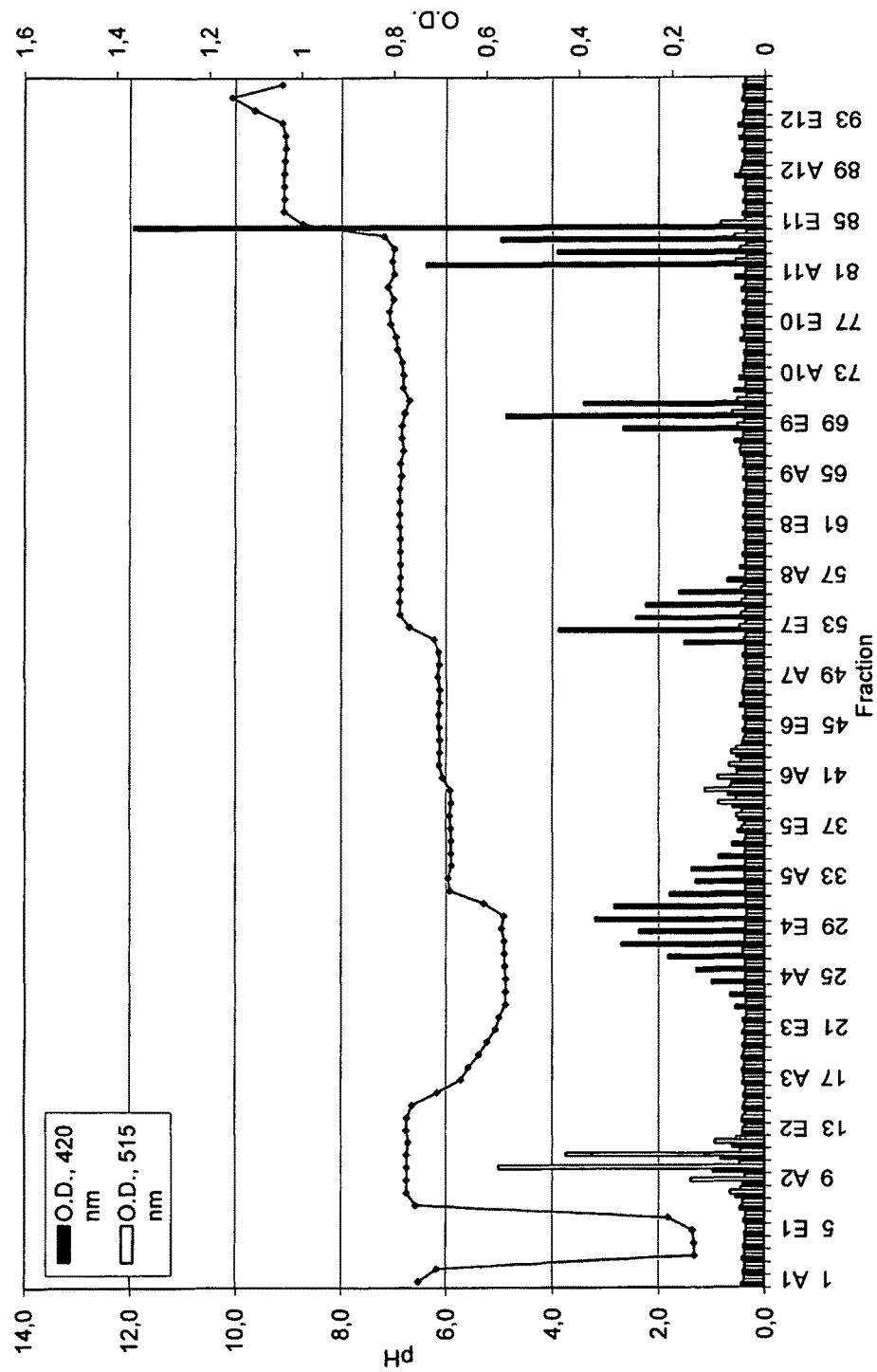
FIG. 7 is a diagram illustrating the result of separating an analyte of interest, namely SPADNS (trisodium 2-(4-sulfophenylazo)-1,8-dihydroxynaphthalene-3,6-disulfonate), from a mixture consisting of a mixture of amphoteric dyes and said non-amphoteric dye SPADNS using the method of the invention realizing a pH step-gradient, whereby the method was carried out as a continuous electrophoresis method. The X-axis indicates the fractions obtained at the fraction points, the Y-axis on the left side indicates the pH value measured in the individual fractions (depicted as full diamonds), and the Y-axis on the right side indicates optical density measured at 420 nm (depicted as full columns)
Figure 8:
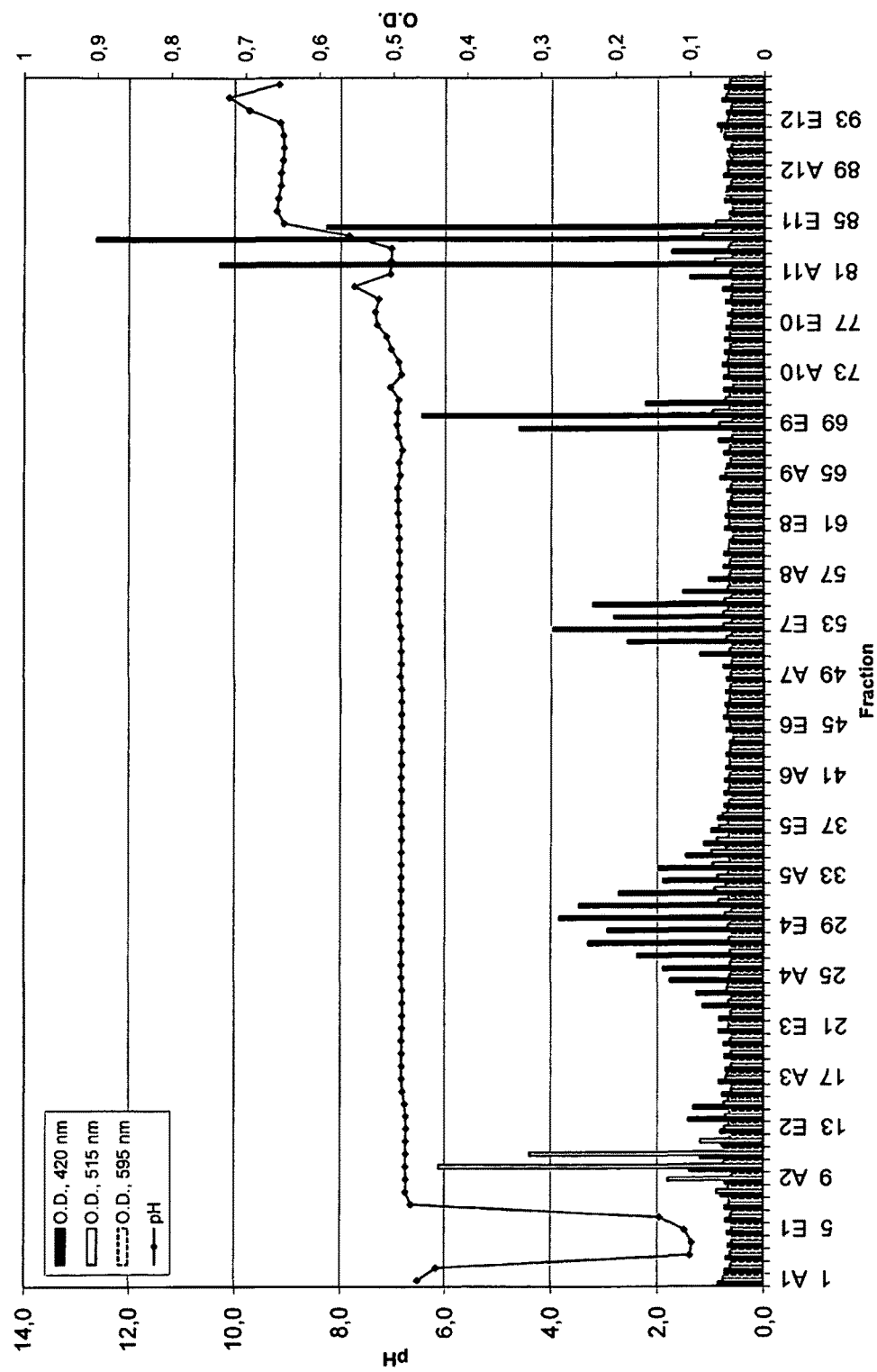
FIG. 8 is a diagram illustrating the result of separating an analyte of interest, namely SPADNS (trisodium 2-(4-sulfophenylazo)-1,8-dihydroxynaphthalene-3,6-disulfonate), from a mixture consisting of a mixture of amphoteric dyes and said non-amphoteric dye SPADNS using a free-flow electrophoresis method of the prior art realizing a constant pH value across the separation medium, whereby the method was carried out as a continuous free-flow electrophoresis method. The X-axis indicates the fractions obtained at the fraction points, the Y-axis on the left side indicates the pH value measured in the individual fractions (depicted as full diamonds), and the Y-axis on the right side indicates optical density measured at 420 nm (depicted as full columns)

Example 2: Separation of an Analyte Consisting of a Mixture of Amphoteric Dyes and Non-Amphoteric Dye SPADNS Analytes consisting of a mixture of amphoteric dyes and non-amphoteric dye SPADNS were subject to the method of the invention realizing a pH step-gradient, whereby the method was carried out as a continuous free-flow electrophoresis method. In order to show the advantage of the method of the invention, the same experiment was carried out using the same method except that no pH gradient was realized, whereby the results are depicted in FIGS. 7 and 8.

The experimental details of the experiments underlying FIGS. 7 and 8 were as follows.

The separation was conducted in a FFE system on a 0.2 mm gap.

The individual separation media and border stabilization media were as follows:

| | |
|---|---|
| Anode border stabilization medium: (inlet 1) | 150 mM HCl<br>300 BISTRIS<br>250 mM Mannitol |
| Individual separation medium 1: (inlets 2&3) | 10 mM BISTRIS<br>250 mM Mannitol<br>adjusted to pH 4.77 with glutamic acid |
| Individual separation medium 2: (inlet 4) | 10 mM glutamic acid<br>250 mM Mannitol<br>adjusted to pH 5.81 with BISTRIS |
| Individual separation medium 3: (inlet 5) | 10 mM glutamic acid<br>250 mM Mannitol<br>adjusted to pH 6.08 with BISTRIS |
| Individual separation medium 4: (inlets 6-8) | 10 mM glutamic acid<br>250 mM Mannitol<br>adjusted to pH 6.87 with BISTRIS |
| Cathode border stabilization medium: | 200 mM triethylamine<br>100 mM EtOH amine<br>50 mM TEA<br>200 mM glutamic acid<br>250 mM Mannitol |
| Counterflow medium: | 250 mM Mannitol |

The sample was injected at individual separation medium 5 with 1200 µl/h; separation was conducted at 1200V and 53 mA continuously at a media speed of ~150 ml/h.

FIG. 8:

The separation was conducted in a FFE system on a 0.2 mm gap.

The individual separation media and border stabilization media were as follows:

| | |
|---|---|
| Anode border stabilization medium: (inlet 1) | 150 mM HCl<br>300 BISTRIS<br>250 mM Mannitol |
| Individual separation medium 1: (inlets 2-5) | 10 mM glutamic acid<br>adjusted to pH 6.86 with BISTRIS<br>250 mM Mannitol |
| Individual separation medium 2: (inlets 6-8) | 10 mM glutamic acid<br>adjusted to pH 6.87 with BISTRIS<br>250 mM Mannitol |
| Cathode border stabilization medium: | 200 mM triethylamine<br>100 mM EtOH amine<br>50 mM TEA<br>200 mM glutamic acid<br>250 mM Mannitol |
| Counterflow medium: | 250 mM Mannitol |

The sample was injected at individual separation medium with 1200 µl/h; separation was conducted at 1200V and 52 mA continuously at a media speed of ~150 ml/h.

The results are shown in FIGS. 7 and 8. FIGS. 7 and 8 display the profile of pH-values and the concentration profiles of the separated analytes inside the sample. In case of the process being continuous FF-zone-electrophoresis, the use of separation media with pH-gradients will give the surplus of quality of separation of the target analytes, marked inside the figures.

Example 3: Separation of a Murine Monoclonal Antibody from a Cell Culture Medium A murine monoclonal antibody was separated from a sample containing the antibody pre-purified by chromatographic techniques (IZE, obtained by using the method of the present invention). Fractions obtained from carrying out the method of the inventions were subject to analysis with PAGIEF (analytical isoelectric focusing on polyacrylamid gels).

The technical details of the method of the invention were as follows.

The separation was conducted in a FFE system on a 0.2 mm gap with a flow rate of the various media of 50 ml/h at a 5 minute interval at 1700V and 120 mA.

20 µl of the sample was diluted with 46.1 separation buffer and injected with 2800 µl/h at S1

The individual separation media and border stabilization media were as follows:

| | |
|---|---|
| Anode border stabilization medium: (inlet 1) | 148 mM HCl<br>150 mM TEA<br>250 mM Mannitol |
| Individual separation medium 1: (inlet 2) | 20 mM TEA<br>20 mM glutamic acid<br>250 mM Mannitol |
| Individual separation medium 2: (inlet 3) | 10 mM TEA<br>10 mM glutamic acid<br>5 mM NaCl<br>250 mM Mannitol |
| Individual separation medium 3: (inlet 4) | 10 mM TEA<br>10 mM glutamic acid<br>250 mM Mannitol<br>adjusted with TEA to pH = 7.53 |
| Individual separation medium 4: (inlet 5) | 10 mM TEA<br>10 mM glutamic acid<br>250 mM Mannitol<br>adjusted with TEA to pH = 7.83 |
| Individual separation medium 5: (inlet 6) | 10 mM TEA<br>10 mM glutamic acid<br>250 mM Mannitol<br>adjusted with TEA to pH = 8.15 |
| Individual separation medium 6: (inlets 7&8) | 50 mM Tris<br>15 mM glutamic acid<br>250 mM Mannitol<br>pH = 8.48 |
| Cathode border stabilizationmedium: (inlet 9) | 200 mM glutamic acid<br>50 mM Tris<br>300 mM Ammediol<br>250 mM Mannitol<br>pH = 8.64 |
| Counterflow medium: | 250 mM Mannitol |

Figure 9:
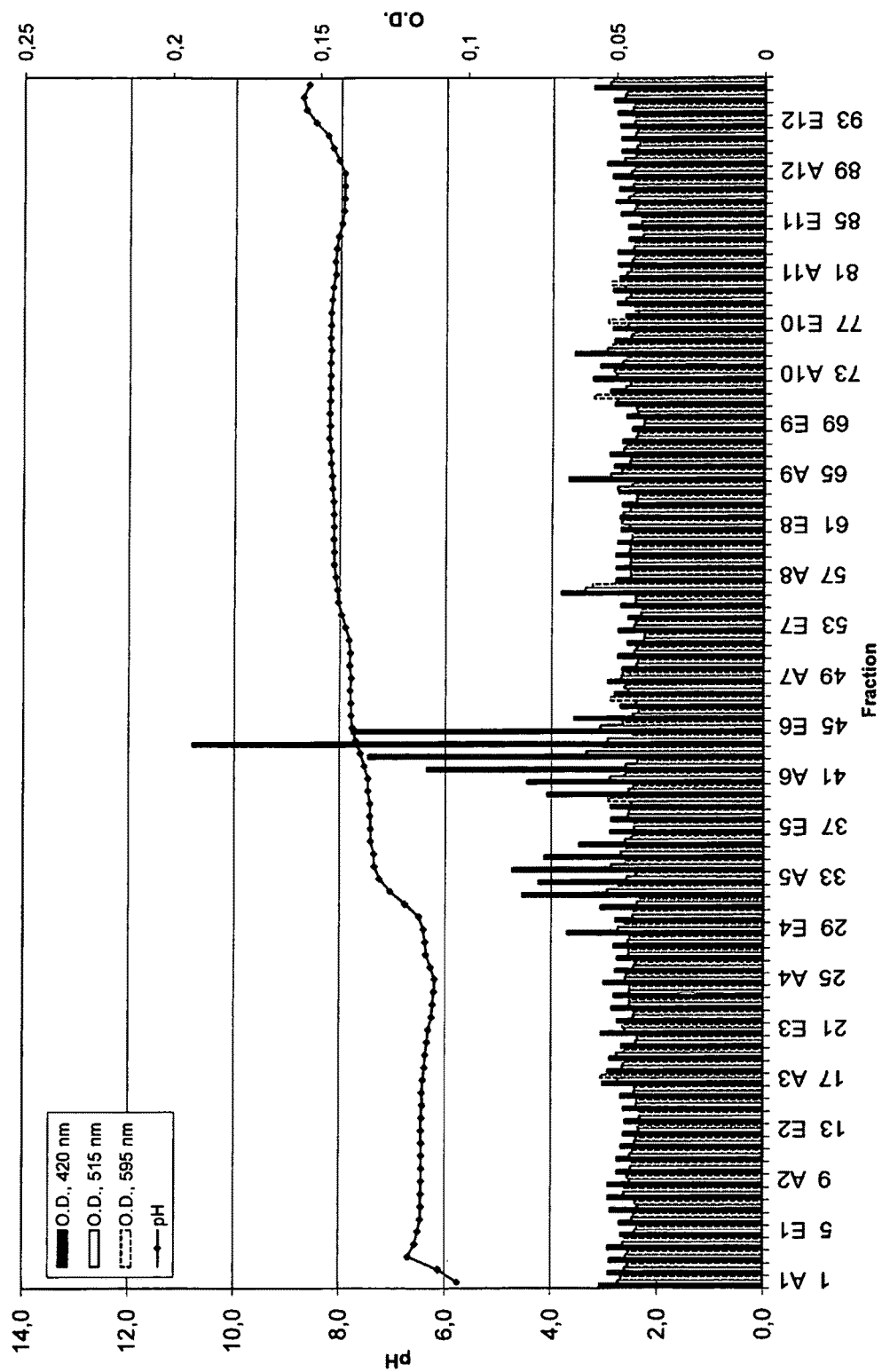
FIG. 9 is a diagram illustrating the result of separation of a monoclonal antibody pre-purified by chromatographic techniques using the method of the invention. The X-axis indicates the fractions obtained at the fraction points, the Y-axis on the left side indicates the pH value measured in the individual fractions (depicted as full diamonds), and the Y-axis on the right side indicates optical densities measured at 420 nm, 515 nm and 595 nm.

The result is shown in FIG. 9. FIG. 9 displays the profile of pH-values and the profiles of concentration of the separated analytes inside the test sample. Following the separation of the test sample, the identical conditions of separation were applied to a sample of the monoclonal antibody.

Figure 10:
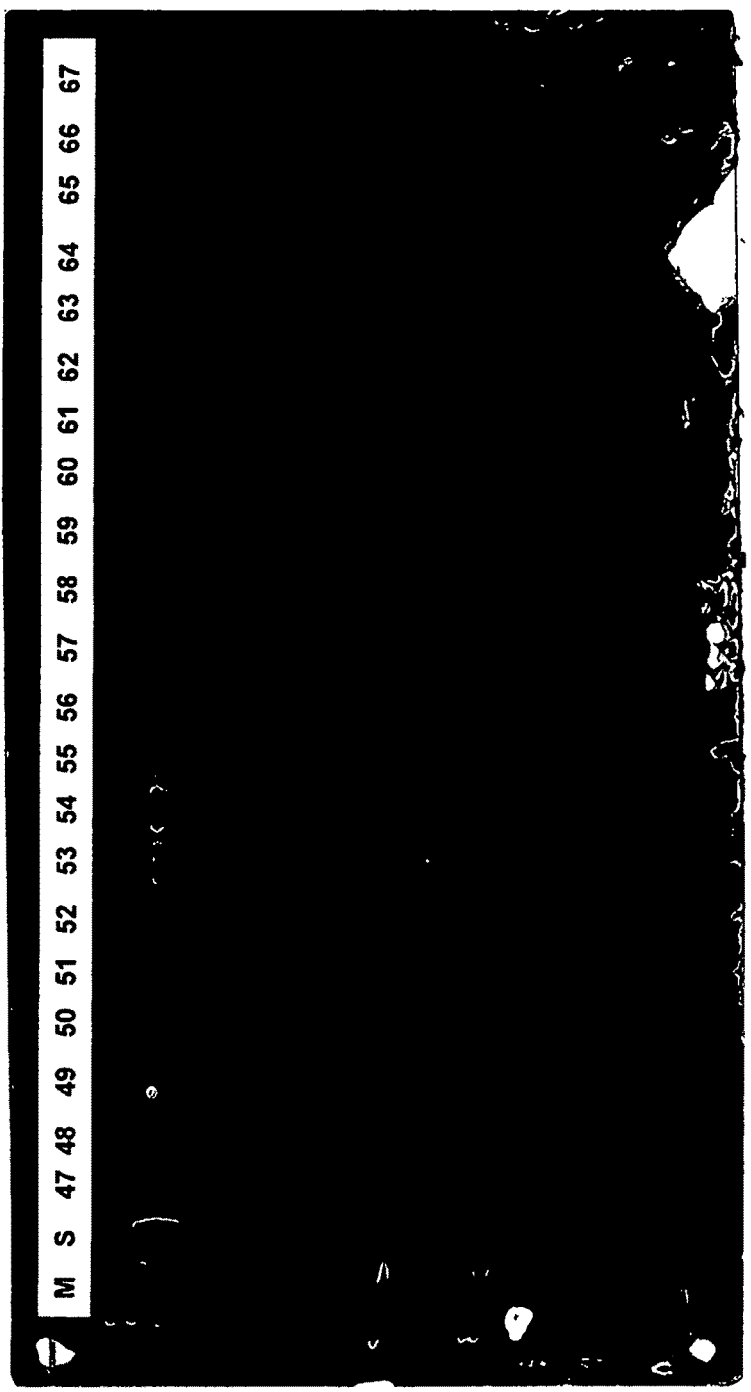
FIG. 10 is the result of a silver stain of an antibody analysed by isoelectric focusing on a PAGE gel after separating the antibody from a sample containing the antibody using the method of the invention.

Fractions 47 to 67 of the FFE run obtained, were subject to the analysis with PAGIEF. The results, as shown FIG. 10, display an excellent quality of separation with a "single band purity" of the separated isoforms of the monoclonal antibody.

Example 4: Separation of Proteins with pI-Value of 7<pI<8.5

Using mixtures of acids and bases with similar values of electrophoretic mobilities protocols can be used for the separation of proteins with a broader range of pI-values. More specifically, the variation of the ratio of the concentrations of the bases allows expanding the pH-range into the alkaline region (pI>7). In a similar approach mixtures of acids with similar values of electrophoretic mobility can be used to expand the pH-range for the separation of proteins with pI values (pI<7).

An example for embodiments of the method of the invention making use of at least one anion of each of two acids and at least one cation of each of two bases is presented in the following.

The technical details of a respective embodiment of the method of the invention were as follows.

The separation was conducted in a FFE system on a 0.2 mm gap with a flow rate of the various media of 50 ml/h at a 5 minute interval at 1700V and 120 mA.

20 µl-50 µl of the sample were injected at S1 or S5

The individual separation media and border stabilization media were as follows:

| | |
|---|---|
| Anode border stabilization medium: (inlet 1) | 148 mM HCl<br>150 mM TEA<br>30 mM TRIS<br>250 mM Mannitol<br>pH = 7.29, alternatively pH = 6.70 or 6.40 |
| Individual separation medium 1: (inlet 2) | 20 mM TEA + 4 mM TRIS<br>20 mM HIBA + 4 mM IBA<br>250 mM Mannitol<br>pH = 6.50, alternatively pH = 6.93 |
| Individual separation medium 2: (inlet 3) | 10 mM TEA + 2 mM TRIS<br>10 mM HIBA + 2 mM IBA<br>5 mM NaCl<br>250 mM Mannitol<br>pH = 6.56, alternatively pH = 7.23 |
| Individual separation medium 3: (inlet 4) | 10 mM TEA + 2 mM TRIS<br>10 mM HIBA + 2 mM IBA<br>250 mM Mannitol<br>adjusted with TEA + TRIS (5:1) to pH = 7.5: |
| Individual separation medium 4: (inlet 5) | 10 mM TEA + 2 mM TRIS<br>10 mM HIBA + 2 mM IBA<br>250 mM Mannitol<br>adjusted with TEA + TRIS (5:1) to pH = 7.83 |
| Individual separation medium 5: (inlet 6) | 10 mM TEA + 2 mM TRIS<br>10 mM HIBA + 2 mM IBA<br>250 mM Mannitol<br>adjusted with TEA + TRIS (5:1) to pH = 8.15 |
| Individual separation medium 6: (inlets 7&8) | 10 mM TEA + 2 mM TRIS<br>15 mM HIBA + 3 mM IBA<br>250 mM Mannitol<br>adjusted with TEA + TRIS (5:1) to pH = 8.48 |
| Cathode border stabilizationmedium: (inlet 9) | 200 mM HIBA + 40 mM IBA<br>50 mM Tris<br>300 mM Ammediol<br>250 mM Mannitol<br>pH = 8.64 |
| Counterflow medium: | 250 mM Mannitol |

HIBA = Hydroxy-Isobutyric-Acid
IBA = Iso-butyric-Acid

The features of the present invention disclosed in the specification, the claims and/or the drawings may both separately and in any combination thereof be material for realizing the invention in various forms thereof.

The invention claimed is:

1. A free-flow electrophoresis method for separating at least one analyte of interest from a mixture of analytes, wherein the method comprises flowing a separation medium through a separation chamber in a flow direction;

applying an electric field in the separation medium by an anode and a cathode, wherein the anode and the cathode are located at a distance from each other and the separation medium flows between the anode and the cathode, and applying the mixture of analytes to the separation medium, whereupon the at least one analyte of interest is separated from the mixture of analytes, or applying the mixture of analytes to the separation medium, and applying an electric field in the separation medium by an anode and a cathode, wherein the anode and the cathode are located at a distance from each other and the separation medium flows between the anode and the cathode, whereupon the at least one analyte of interest is separated from the mixture of analytes;

collecting fractions of the separation medium with at least one fraction comprising the at least one analyte of interest separated from the mixture of analytes;

characterized in that the separation medium comprises two or more individual separation media, wherein the two or more individual separation media differ in their pH value, and wherein each of the two or more individual separation media comprise at least one anion of at least one acid and at least one cation of at least one base, wherein the at least one acid is the same in each of the two or more individual separation media and the at least one base is the same in each of the two or more individual separation media;

the at least one anion of the at least one acid is the same in each of the two or more individual separation media and the at least one cation of the at least one base is the same in each of the two or more individual separation media; and if the analyte of interest has a pI of >7, the analyte of interest is separated at an optimum pH range $pH_{opt}$, wherein $pH_{opt}$ is determined as follows:

$$pI-0.6 < pH_{opt} \leq pI \text{ or}$$

if the analyte of interest has a pI of <7, the analyte of interest is separated at an optimum pH range $pH_{opt}$, wherein $pH_{opt}$ is determined as follows:

$$pI \leq pH_{opt} < pI+0.6.$$

2. The free-flow electrophoresis method of claim 1, wherein the pH value of the two or more individual separation media is set prior to carrying out the free-flow electrophoresis method.

3. The method of claim 1, wherein the pH value of the two or more separation media increases from the anode to the cathode.

4. The method of claim 1, wherein the separation medium comprises 2, 3, 4, 5, 6, 7, 8, 9, 10, 11, 12, 13, 14, 15, 16, 17, 18, 19, 20 or more individual separation media.

5. The method of claim 1, wherein either (i) the pKa value of the acid is from about 3 to 8, (ii) the pKa value of the base is from about 4 to 10, or (iii) the pKa value of the acid is from about 3 to 8 and the pKa value of the base is from about 4 to 10.

6. The method of claim 1, wherein the concentration of the anion in at least one or each of the at least two individual separation media is from about 3-100 mM.

7. The method of claim 1, wherein in case of a cationic separation the concentration of the cation in at least one or each of the at least two individual separation media is from 5-50 mM.

8. The method of claim 1, wherein in case of an anionic separation the concentration of the anion in at least one or each of the at least two individual separation media is from 5-50 mM.

9. The method of claim 1, wherein either (i) the concentration of the acid is up to 500 mM at the pH of the individual separation medium at the cathode or at the pH of the border stabilization medium at the cathode, (ii) the concentration of the base is up tp 500 mM at the pH of the individual separation medium at the anode or at the pH of the border stabilization medium at the anode, or (iii) the concentration of the acid is up to 500 mM at the pH of the individual separation medium at the cathode or at the pH of the border stabilization medium at the cathode and the concentration of the base is up to 500 mM at the pH of the individual separation medium at the anode of at the pH of the border stabilization medium at the anode.

10. The method of claim 1, wherein the anion bears a single negative charge at the pH value of the individual separation media and/or wherein the cation bears a single positive charge at the pH value of the individual separation media.

11. The method of claim 1, wherein each of the two or more individual separation media comprises at least one anion of two or more acids.

12. The method of claim 1, wherein the free-flow electrophoresis method is interval free-flow electrophoresis method.

13. The method of claim 1, wherein the free-flow electrophoresis method is a continuous free-flow electrophoresis method.

14. The method of claim 1, wherein the analytes are selected from the group comprising cells, cell compartments, nanobeads, nanodiscs, viruses and any compounds.

15. The method of claim 14, wherein the compounds are biological and chemical compounds.

16. The method of claim 15, wherein the compounds are charged biological and chemical compounds.

17. A free-flow electrophoresis method for separating at least one analyte of interest from a mixture of analytes, wherein the method comprises:
flowing a separation medium through a separation chamber in a flow direction;
applying an electric field in the separation medium by an anode and a cathode, wherein the anode and the cathode are located at a distance from each other and the separation medium flows between the anode and the cathode, and applying the mixture of analytes to the separation medium, whereupon the at least one analyte of interest is separated from the mixture of analytes,
or
applying the mixture of analytes to the separation medium, and applying an electric field in the separation medium by an anode and a cathode, wherein the anode and the cathode are located at a distance from each other and the separation medium flows between the anode and the cathode, whereupon the at least one analyte of interest is separated from the mixture of analytes; and
collecting fractions of the separation medium with at least one fraction comprising the at least one analyte of interest separated from the mixture of analytes;
characterized in that
the separation medium comprises two or more individual separation media, wherein the two or more individual separation media differ in their pH value, and wherein each of the two or more individual separation media comprise at least one anion of at least one acid and at least one cation of at least one base, wherein the at least one acid is the same in each of the two or more individual separation media and the at least one base is the same in each of the two or more individual separation media,
wherein each of the two or more individual separation media comprises at least one cation of two or more bases.

18. A free-flow electrophoresis method for separating at least one analyte of interest from a mixture of analytes, wherein the method comprises
flowing a separation medium through a separation chamber in a flow direction;
applying an electric field in the separation medium by an anode and a cathode, wherein the anode and the cathode are located at a distance from each other and the separation medium flows between the anode and the cathode, and applying the mixture of analytes to the separation medium, whereupon the at least one analyte of interest is separated from the mixture of analytes,
or
applying the mixture of analytes to the separation medium, and applying an electric field in the separation medium by an anode and a cathode, wherein the anode and the cathode are located at a distance from each other and the separation medium flows between the anode and the cathode, whereupon the at least one analyte of interest is separated from the mixture of analytes; and
collecting fractions of the separation medium with at least one fraction comprising the at least one analyte of interest separated from the mixture of analytes;
characterized in that
the separation medium comprises two or more individual separation media, wherein the two or more individual separation media differ in their pH value, and wherein each of the two or more individual separation media comprise at least one anion of at least one acid and at least one cation of at least one base, wherein the at least one acid is the same in each of the two or more individual separation media and the at least one base is the same in each of the two or more individual separation media, wherein each of the two or more individual separation media comprises at least one anion of two or more acids and at least one cation of two or more bases,
wherein each of the two or more individual separation media comprises at least one anion of two or more acids and at least one cation of two or more bases.

* * * * *